United States Patent
Nageswaran et al.

(10) Patent No.: US 10,945,867 B2
(45) Date of Patent: *Mar. 16, 2021

(54) COUPLING UNITS FOR MEDICAL DEVICE DELIVERY SYSTEMS

(71) Applicant: Covidien LP, Mansfield, MA (US)

(72) Inventors: Ashok Nageswaran, Irvine, CA (US); Cong Dang, Garden Grove, CA (US); Aaron Barrett, San Clemente, CA (US); James Phan, Santa Ana, CA (US)

(73) Assignee: COVIDIEN LP, Mansfield, MA (US)

( * ) Notice: Subject to any disclaimer, the term of this patent is extended or adjusted under 35 U.S.C. 154(b) by 73 days.

This patent is subject to a terminal disclaimer.

(21) Appl. No.: 16/459,118

(22) Filed: Jul. 1, 2019

(65) Prior Publication Data

US 2019/0336312 A1 Nov. 7, 2019

Related U.S. Application Data

(63) Continuation of application No. 15/410,444, filed on Jan. 19, 2017, now Pat. No. 10,376,396.

(51) Int. Cl.
*A61F 2/90* (2013.01)
*A61F 2/95* (2013.01)
(Continued)

(52) U.S. Cl.
CPC .................. *A61F 2/90* (2013.01); *A61F 2/95* (2013.01); *A61F 2/966* (2013.01); *A61F 2/86* (2013.01);
(Continued)

(58) Field of Classification Search
CPC ........ A61F 2002/823; A61F 2002/9505; A61F 2002/9665; A61F 2230/0069; A61F 2/86;
(Continued)

(56) References Cited

U.S. PATENT DOCUMENTS

| | | |
|---|---|---|
| 3,416,531 A | 12/1968 | Lowell |
| 4,364,391 A | 12/1982 | Toye |

(Continued)

FOREIGN PATENT DOCUMENTS

| | | |
|---|---|---|
| CN | 104582643 A | 4/2015 |
| CN | 105232195 A | 1/2016 |

(Continued)

OTHER PUBLICATIONS

Search Report dated Mar. 24, 2020, CN Application No. 201880007614.9, 10 pages.

*Primary Examiner* — George J Ulsh
*Assistant Examiner* — Andrew P. Restaino
(74) *Attorney, Agent, or Firm* — Fortem IP LLP; Matthew Lincicum

(57) ABSTRACT

A stent coupler for use with a medical device delivery system is disclosed. A stent delivery system includes a core member having a distal segment and a coupler positioned about the core member distal segment. the coupler is rotatably coupled to the core member and includes a rigid plate having a first end surface, a second end surface, and a side surface extending between the first and second end surfaces, the side surface comprising one or more projections separated by recesses. The delivery system further includes a stent extending along the core member distal segment such that an inner surface of the stent is engaged by the one or more projections of the engagement member.

22 Claims, 7 Drawing Sheets

(51) Int. Cl.
*A61F 2/966* (2013.01)
*A61F 2/82* (2013.01)
*A61F 2/86* (2013.01)

(52) U.S. Cl.
CPC . *A61F 2002/823* (2013.01); *A61F 2002/9505* (2013.01); *A61F 2002/9665* (2013.01); *A61F 2230/0069* (2013.01)

(58) Field of Classification Search
CPC .... A61F 2/90; A61F 2/95; A61F 2/966; A61F 2002/9511; A61F 2002/9517; A61F 2/06; A61F 2/2436; A61F 2/962
See application file for complete search history.

(56) References Cited

U.S. PATENT DOCUMENTS

| | | |
|---|---|---|
| 4,425,919 A | 1/1984 | Alston, Jr. et al. |
| 4,516,972 A | 5/1985 | Samson |
| 4,723,936 A | 2/1988 | Buchbinder et al. |
| 4,877,031 A | 10/1989 | Conway et al. |
| 4,990,151 A | 2/1991 | Wallsten |
| 5,011,478 A | 4/1991 | Cope |
| 5,026,377 A | 6/1991 | Burton et al. |
| 5,037,404 A | 8/1991 | Gold et al. |
| 5,061,275 A | 10/1991 | Wallsten et al. |
| 5,098,393 A | 3/1992 | Amplatz et al. |
| 5,108,411 A | 4/1992 | Mckenzie |
| 5,147,370 A | 9/1992 | Mcnamara et al. |
| 5,178,158 A | 1/1993 | De Toledo |
| 5,201,316 A | 4/1993 | Pomeranz et al. |
| 5,209,734 A | 5/1993 | Hurley et al. |
| 5,279,562 A | 1/1994 | Sirhan et al. |
| 5,279,596 A | 1/1994 | Castaneda et al. |
| 5,292,311 A | 3/1994 | Cope |
| 5,318,032 A | 6/1994 | Lonsbury et al. |
| 5,318,525 A | 6/1994 | West et al. |
| 5,318,529 A | 6/1994 | Kontos |
| 5,358,493 A | 10/1994 | Schweich, Jr. et al. |
| 5,382,259 A | 1/1995 | Phelps et al. |
| 5,403,292 A | 4/1995 | Ju |
| 5,437,288 A | 8/1995 | Schwartz et al. |
| 5,445,646 A | 8/1995 | Euteneuer et al. |
| 5,454,795 A | 10/1995 | Samson |
| 5,458,605 A | 10/1995 | Klemm |
| 5,474,563 A | 12/1995 | Myler et al. |
| 5,478,349 A | 12/1995 | Nicholas |
| 5,484,444 A | 1/1996 | Braunschweiler et al. |
| 5,496,294 A | 3/1996 | Hergenrother et al. |
| 5,499,975 A | 3/1996 | Cope et al. |
| 5,522,822 A | 6/1996 | Phelps et al. |
| 5,531,721 A | 7/1996 | Pepin et al. |
| 5,534,007 A | 7/1996 | St Germain et al. |
| 5,545,209 A | 8/1996 | Roberts et al. |
| 5,554,139 A | 9/1996 | Okajima |
| 5,569,220 A | 10/1996 | Webster, Jr. |
| 5,571,135 A | 11/1996 | Fraser et al. |
| 5,573,520 A | 11/1996 | Schwartz et al. |
| 5,584,821 A | 12/1996 | Hobbs et al. |
| 5,599,325 A | 2/1997 | Ju et al. |
| 5,599,326 A | 2/1997 | Carter |
| 5,601,539 A | 2/1997 | Corso, Jr. |
| 5,636,641 A | 6/1997 | Fariabi |
| 5,645,559 A | 7/1997 | Hachtman et al. |
| 5,658,264 A | 8/1997 | Samson |
| 5,662,622 A | 9/1997 | Gore et al. |
| 5,676,659 A | 10/1997 | Mcgurk |
| 5,695,483 A | 12/1997 | Samson |
| 5,695,499 A | 12/1997 | Helgerson et al. |
| 5,702,373 A | 12/1997 | Samson |
| 5,702,418 A | 12/1997 | Ravenscroft |
| 5,704,926 A | 1/1998 | Sutton |
| 5,709,703 A | 1/1998 | Lukic et al. |
| 5,711,909 A | 1/1998 | Gore et al. |
| 5,725,513 A | 3/1998 | Ju et al. |
| 5,725,571 A | 3/1998 | Imbert et al. |
| 5,728,063 A | 3/1998 | Preissman et al. |
| 5,741,429 A | 4/1998 | Donadio, III et al. |
| 5,743,876 A | 4/1998 | Swanson |
| 5,759,173 A | 6/1998 | Preissman et al. |
| 5,776,141 A | 7/1998 | Klein et al. |
| 5,782,811 A | 7/1998 | Samson et al. |
| 5,791,036 A | 8/1998 | Goodin et al. |
| 5,824,041 A | 10/1998 | Lenker et al. |
| 5,833,632 A | 11/1998 | Jacobsen et al. |
| 5,836,925 A | 11/1998 | Soltesz |
| 5,836,926 A | 11/1998 | Peterson et al. |
| 5,851,203 A | 12/1998 | Van Muiden |
| 5,853,400 A | 12/1998 | Samson |
| 5,873,866 A | 2/1999 | Kondo et al. |
| 5,876,386 A | 3/1999 | Samson |
| 5,891,112 A | 4/1999 | Samson |
| 5,897,529 A | 4/1999 | Ponzi |
| 5,897,537 A | 4/1999 | Berg et al. |
| 5,902,290 A | 5/1999 | Peacock, III et al. |
| 5,906,605 A | 5/1999 | Coxum |
| 5,935,161 A | 8/1999 | Robinson et al. |
| 5,938,653 A | 8/1999 | Pepin |
| 5,951,494 A | 9/1999 | Wang et al. |
| 5,951,539 A | 9/1999 | Nita et al. |
| 5,961,510 A | 10/1999 | Fugoso et al. |
| 5,968,053 A | 10/1999 | Revelas |
| 5,968,069 A | 10/1999 | Dusbabek et al. |
| 5,971,975 A | 10/1999 | Mills et al. |
| 6,017,323 A | 1/2000 | Chee |
| 6,030,371 A | 2/2000 | Pursley |
| 6,045,547 A | 4/2000 | Ren et al. |
| 6,053,903 A | 4/2000 | Samson |
| 6,053,904 A | 4/2000 | Scribner et al. |
| 6,077,258 A | 6/2000 | Lange et al. |
| 6,077,295 A | 6/2000 | Limon et al. |
| 6,077,297 A | 6/2000 | Robinson et al. |
| 6,083,152 A | 7/2000 | Strong |
| 6,093,177 A | 7/2000 | Javier, Jr. et al. |
| 6,105,651 A | 8/2000 | Leanna |
| 6,106,510 A | 8/2000 | Lunn et al. |
| 6,106,540 A | 8/2000 | Dehdashtian et al. |
| 6,123,723 A | 9/2000 | Konya et al. |
| 6,126,685 A | 10/2000 | Lenker et al. |
| 6,135,992 A | 10/2000 | Wang |
| 6,149,680 A | 11/2000 | Shelso et al. |
| 6,152,912 A | 11/2000 | Jansen et al. |
| 6,152,944 A | 11/2000 | Holman et al. |
| 6,159,219 A | 12/2000 | Ren |
| 6,165,163 A | 12/2000 | Chien et al. |
| 6,165,166 A | 12/2000 | Samuelson et al. |
| 6,171,295 B1 | 1/2001 | Garabedian et al. |
| 6,171,296 B1 | 1/2001 | Chow |
| 6,171,297 B1 | 1/2001 | Pedersen et al. |
| 6,186,986 B1 | 2/2001 | Berg et al. |
| 6,193,739 B1 | 2/2001 | Chevillon et al. |
| 6,197,015 B1 | 3/2001 | Wilson |
| 6,217,565 B1 | 4/2001 | Cohen |
| 6,217,566 B1 | 4/2001 | Ju et al. |
| 6,251,132 B1 | 6/2001 | Ravenscroft et al. |
| 6,258,080 B1 | 7/2001 | Samson |
| 6,264,683 B1 | 7/2001 | Stack et al. |
| 6,287,315 B1 | 9/2001 | Wijeratne et al. |
| 6,325,807 B1 | 12/2001 | Que |
| 6,350,278 B1 | 2/2002 | Lenker et al. |
| 6,355,027 B1 | 3/2002 | Le et al. |
| 6,358,238 B1 | 3/2002 | Sherry |
| 6,358,460 B1 | 3/2002 | Hunt, Jr. et al. |
| 6,368,316 B1 | 4/2002 | Jansen et al. |
| 6,371,953 B1 | 4/2002 | Beyar et al. |
| 6,383,171 B1 | 5/2002 | Gifford et al. |
| 6,387,118 B1 | 5/2002 | Hanson |
| 6,389,087 B1 | 5/2002 | Heinonen et al. |
| 6,395,008 B1 | 5/2002 | Ellis et al. |
| 6,395,017 B1 | 5/2002 | Dwyer et al. |
| 6,398,791 B1 | 6/2002 | Que et al. |
| 6,419,693 B1 | 7/2002 | Fariabi |
| 6,425,898 B1 | 7/2002 | Wilson et al. |
| 6,428,552 B1 | 8/2002 | Sparks |

(56) References Cited

U.S. PATENT DOCUMENTS

| | | | |
|---|---|---|---|
| 6,443,971 | B1 | 9/2002 | Boylan et al. |
| 6,458,075 | B1 | 10/2002 | Sugiyama et al. |
| 6,464,684 | B1 | 10/2002 | Galdonik |
| 6,468,298 | B1 | 10/2002 | Pelton |
| 6,475,184 | B1 | 11/2002 | Wang et al. |
| 6,494,907 | B1 | 12/2002 | Bulver |
| 6,508,804 | B2 | 1/2003 | Sarge et al. |
| 6,508,805 | B1 | 1/2003 | Garabedian et al. |
| 6,508,806 | B1 | 1/2003 | Hoste |
| 6,517,547 | B1 | 2/2003 | Feeser et al. |
| 6,554,820 | B1 | 4/2003 | Wendlandt et al. |
| 6,562,021 | B1 | 5/2003 | Derbin et al. |
| 6,562,063 | B1 | 5/2003 | Euteneuer et al. |
| 6,576,006 | B2 | 6/2003 | Limon et al. |
| 6,582,460 | B1 | 6/2003 | Cryer |
| 6,589,227 | B2 | 7/2003 | Soenderskov |
| 6,602,271 | B2 | 8/2003 | Adams et al. |
| 6,607,551 | B1 | 8/2003 | Sullivan et al. |
| 6,622,367 | B1 | 9/2003 | Bolduc et al. |
| 6,635,047 | B2 | 10/2003 | Forsberg |
| 6,638,245 | B2 | 10/2003 | Miller et al. |
| 6,641,564 | B1 | 11/2003 | Kraus |
| 6,648,654 | B1 | 11/2003 | Hembree |
| 6,648,874 | B2 | 11/2003 | Parisi et al. |
| 6,652,508 | B2 | 11/2003 | Griffin et al. |
| 6,663,614 | B1 | 12/2003 | Carter |
| 6,669,719 | B2 | 12/2003 | Wallace et al. |
| 6,689,120 | B1 | 2/2004 | Gerdts |
| 6,699,274 | B2 | 3/2004 | Stinson |
| 6,702,782 | B2 | 3/2004 | Miller et al. |
| 6,706,055 | B2 | 3/2004 | Douk et al. |
| 6,716,207 | B2 | 4/2004 | Farnholtz |
| 6,726,659 | B1 | 4/2004 | Stocking et al. |
| 6,764,504 | B2 | 7/2004 | Wang et al. |
| 6,808,529 | B2 | 10/2004 | Fulkerson |
| 6,814,749 | B2 | 11/2004 | Cox et al. |
| 6,815,325 | B2 | 11/2004 | Ishii |
| 6,817,995 | B1 | 11/2004 | Halpern |
| 6,830,575 | B2 | 12/2004 | Stenzel et al. |
| 6,837,890 | B1 | 1/2005 | Chludzinski et al. |
| 6,843,802 | B1 | 1/2005 | Villalobos et al. |
| 6,858,024 | B1 | 2/2005 | Berg et al. |
| 6,866,660 | B2 | 3/2005 | Garabedian et al. |
| 6,866,679 | B2 | 3/2005 | Kusleika |
| 6,932,837 | B2 | 8/2005 | Amplatz et al. |
| 6,939,353 | B2 | 9/2005 | Que et al. |
| 6,945,970 | B2 | 9/2005 | Pepin |
| 6,960,227 | B2 | 11/2005 | Jones et al. |
| 6,984,963 | B2 | 1/2006 | Pidutti et al. |
| 6,989,024 | B2 | 1/2006 | Hebert et al. |
| 7,001,369 | B2 | 2/2006 | Griffin et al. |
| 7,011,675 | B2 | 3/2006 | Hemerick et al. |
| 7,025,758 | B2 | 4/2006 | Klint |
| 7,074,236 | B2 | 7/2006 | Rabkin et al. |
| 7,104,979 | B2 | 9/2006 | Jansen et al. |
| 7,147,656 | B2 | 12/2006 | Andreas et al. |
| 7,156,860 | B2 | 1/2007 | Wallsten |
| 7,163,523 | B2 | 1/2007 | Devens, Jr. et al. |
| 7,166,088 | B2 | 1/2007 | Heuser |
| 7,166,099 | B2 | 1/2007 | Devens, Jr. |
| 7,166,100 | B2 | 1/2007 | Jordan et al. |
| 7,172,575 | B2 | 2/2007 | El-nounou et al. |
| 7,223,263 | B1 | 5/2007 | Seno |
| 7,228,878 | B2 | 6/2007 | Chen et al. |
| 7,306,624 | B2 | 12/2007 | Yodfat et al. |
| 7,323,000 | B2 | 1/2008 | Monstdt et al. |
| 7,331,948 | B2 | 2/2008 | Skarda |
| 7,357,812 | B2 | 4/2008 | Andreas et al. |
| 7,371,248 | B2 | 5/2008 | Dapolito et al. |
| 7,402,151 | B2 | 7/2008 | Rosenman et al. |
| 7,404,820 | B2 | 7/2008 | Mazzocchi et al. |
| 7,427,288 | B2 | 9/2008 | Sater |
| 7,438,712 | B2 | 10/2008 | Chouinard |
| 7,445,684 | B2 | 11/2008 | Pursley |
| 7,473,271 | B2 | 1/2009 | Gunderson |
| 7,473,272 | B2 | 1/2009 | Pryor |
| 7,481,804 | B2 | 1/2009 | Devens, Jr. |
| 7,507,229 | B2 | 3/2009 | Hewitt et al. |
| 7,524,322 | B2 | 4/2009 | Monstadt et al. |
| 7,556,634 | B2 | 7/2009 | Lee et al. |
| 7,556,710 | B2 | 7/2009 | Leeflang et al. |
| 7,569,046 | B2 | 8/2009 | Zhou |
| 7,572,290 | B2 | 8/2009 | Yodfat et al. |
| 7,582,079 | B2 | 9/2009 | Wendlandt et al. |
| 7,597,830 | B2 | 10/2009 | Zhou |
| 7,621,904 | B2 | 11/2009 | Mcferran et al. |
| 7,641,646 | B2 | 1/2010 | Kennedy, II |
| 7,651,520 | B2 | 1/2010 | Fischell et al. |
| 7,655,031 | B2 | 2/2010 | Tenne et al. |
| 7,674,411 | B2 | 3/2010 | Berg et al. |
| 7,691,138 | B2 | 4/2010 | Stenzel et al. |
| 7,708,704 | B2 | 5/2010 | Mitelberg et al. |
| 7,717,953 | B2 | 5/2010 | Kaplan et al. |
| 7,740,652 | B2 | 6/2010 | Gerdts et al. |
| 7,758,624 | B2 | 7/2010 | Dorn et al. |
| 7,766,820 | B2 | 8/2010 | Core |
| 7,766,896 | B2 | 8/2010 | Kornkven et al. |
| 7,780,646 | B2 | 8/2010 | Farnholtz |
| 7,815,600 | B2 | 10/2010 | Al-marashi et al. |
| 7,815,608 | B2 | 10/2010 | Schafersman et al. |
| 7,815,628 | B2 | 10/2010 | Devens, Jr. |
| 7,828,790 | B2 | 11/2010 | Griffin |
| 7,867,267 | B2 | 1/2011 | Sullivan et al. |
| 7,879,022 | B2 | 2/2011 | Bonnette et al. |
| 7,935,140 | B2 | 5/2011 | Griffin |
| 7,942,925 | B2 | 5/2011 | Yodfat et al. |
| 7,955,370 | B2 | 6/2011 | Gunderson |
| 7,981,148 | B2 | 7/2011 | Aguilar et al. |
| 7,993,385 | B2 | 8/2011 | Levine et al. |
| 8,025,692 | B2 | 9/2011 | Feeser |
| 8,034,095 | B2 | 10/2011 | Randolph et al. |
| 8,042,720 | B2 | 10/2011 | Shifrin et al. |
| 8,048,104 | B2 | 11/2011 | Monstadt et al. |
| 8,066,754 | B2 | 11/2011 | Malewicz |
| 8,083,791 | B2 | 12/2011 | Kaplan et al. |
| 8,088,140 | B2 | 1/2012 | Ferrera et al. |
| 8,092,508 | B2 | 1/2012 | Leynov et al. |
| 8,109,987 | B2 | 2/2012 | Kaplan et al. |
| 8,133,266 | B2 | 3/2012 | Thomas et al. |
| 8,147,534 | B2 | 4/2012 | Berez et al. |
| 8,187,314 | B2 | 5/2012 | Davis et al. |
| 8,257,432 | B2 | 9/2012 | Kaplan et al. |
| 8,298,276 | B2 | 10/2012 | Ozawa et al. |
| 8,317,850 | B2 | 11/2012 | Kusleika |
| 8,337,543 | B2 | 12/2012 | Jordan et al. |
| 8,366,763 | B2 | 2/2013 | Davis et al. |
| 8,382,818 | B2 | 2/2013 | Davis et al. |
| 8,480,701 | B2 | 7/2013 | Monstadt |
| 8,579,958 | B2 | 11/2013 | Kusleika |
| 8,591,566 | B2 | 11/2013 | Newell et al. |
| 8,597,321 | B2 | 12/2013 | Monstadt et al. |
| 8,636,760 | B2 | 1/2014 | Garcia et al. |
| 8,679,172 | B2 | 3/2014 | Dorn et al. |
| 8,790,387 | B2 | 7/2014 | Nguyen et al. |
| 8,858,613 | B2 | 10/2014 | Cragg et al. |
| 8,968,383 | B1 | 3/2015 | Johnson et al. |
| 9,393,141 | B2 | 7/2016 | Gerdts et al. |
| 9,439,795 | B2 | 9/2016 | Wang et al. |
| 2001/0020173 | A1 | 9/2001 | Klumb et al. |
| 2001/0027310 | A1 | 10/2001 | Parisi et al. |
| 2001/0029362 | A1 | 10/2001 | Sirhan et al. |
| 2001/0044591 | A1 | 11/2001 | Stevens et al. |
| 2001/0049547 | A1 | 12/2001 | Moore |
| 2002/0029046 | A1 | 3/2002 | Lorentzen et al. |
| 2002/0045929 | A1 | 4/2002 | Diaz |
| 2002/0049412 | A1 | 4/2002 | Madrid et al. |
| 2002/0072789 | A1 | 6/2002 | Hackett et al. |
| 2002/0107526 | A1 | 8/2002 | Greenberg et al. |
| 2002/0111666 | A1 | 8/2002 | Hart et al. |
| 2002/0138128 | A1 | 9/2002 | Stiger et al. |
| 2002/0156459 | A1 | 10/2002 | Ye et al. |
| 2002/0156460 | A1 | 10/2002 | Ye et al. |
| 2002/0165523 | A1 | 11/2002 | Chin et al. |
| 2002/0188342 | A1 | 12/2002 | Rykhus et al. |

(56) References Cited

U.S. PATENT DOCUMENTS

| | | |
|---|---|---|
| 2003/0004539 A1 | 1/2003 | Linder et al. |
| 2003/0009208 A1 | 1/2003 | Snyder et al. |
| 2003/0050600 A1 | 3/2003 | Ressemann et al. |
| 2003/0191451 A1 | 10/2003 | Gilmartin |
| 2003/0212410 A1 | 11/2003 | Stenzel et al. |
| 2003/0212430 A1 | 11/2003 | Bose et al. |
| 2004/0024416 A1 | 2/2004 | Yodfat et al. |
| 2004/0092879 A1 | 5/2004 | Kraus et al. |
| 2004/0111095 A1 | 6/2004 | Gordon et al. |
| 2004/0143239 A1 | 7/2004 | Zhou et al. |
| 2004/0147903 A1 | 7/2004 | Latini |
| 2004/0158230 A1 | 8/2004 | Hunn et al. |
| 2004/0181174 A2 | 9/2004 | Davis et al. |
| 2004/0193140 A1 | 9/2004 | Griffin et al. |
| 2004/0193243 A1 | 9/2004 | Mangiardi et al. |
| 2004/0204749 A1 | 10/2004 | Gunderson |
| 2004/0220585 A1 | 11/2004 | Nikolchev et al. |
| 2004/0230285 A1 | 11/2004 | Gifford et al. |
| 2004/0260271 A1 | 12/2004 | Huyser et al. |
| 2004/0260384 A1 | 12/2004 | Allen |
| 2005/0033403 A1 | 2/2005 | Ward et al. |
| 2005/0070794 A1 | 3/2005 | Deal et al. |
| 2005/0090802 A1 | 4/2005 | Connors et al. |
| 2005/0096724 A1 | 5/2005 | Stenzel et al. |
| 2005/0119719 A1 | 6/2005 | Wallace et al. |
| 2005/0125051 A1 | 6/2005 | Eidenschink et al. |
| 2005/0131449 A1 | 6/2005 | Salahieh et al. |
| 2005/0143773 A1 | 6/2005 | Abrams et al. |
| 2005/0149160 A1 | 7/2005 | Mcferran |
| 2005/0182388 A1 | 8/2005 | Garabedian et al. |
| 2005/0182475 A1 | 8/2005 | Jen et al. |
| 2005/0228361 A1 | 10/2005 | Tremaglio |
| 2005/0240254 A1 | 10/2005 | Austin |
| 2005/0273149 A1 | 12/2005 | Tran et al. |
| 2005/0277949 A1 | 12/2005 | Que et al. |
| 2006/0030835 A1 | 2/2006 | Sherman et al. |
| 2006/0036309 A1 | 2/2006 | Hebert et al. |
| 2006/0058865 A1 | 3/2006 | Case et al. |
| 2006/0064123 A1 | 3/2006 | Bonnette et al. |
| 2006/0074477 A1 | 4/2006 | Berthiaume et al. |
| 2006/0089618 A1 | 4/2006 | Mcferran et al. |
| 2006/0095050 A1 | 5/2006 | Hartley et al. |
| 2006/0100687 A1 | 5/2006 | Fahey et al. |
| 2006/0100688 A1 | 5/2006 | Jordan et al. |
| 2006/0116750 A1 | 6/2006 | Hebert et al. |
| 2006/0129166 A1 | 6/2006 | Lavelle |
| 2006/0178698 A1 | 8/2006 | Mcintyre et al. |
| 2006/0184226 A1 | 8/2006 | Austin |
| 2006/0212042 A1 | 9/2006 | Lamport et al. |
| 2006/0217682 A1 | 9/2006 | Stivland et al. |
| 2006/0235502 A1 | 10/2006 | Belluche et al. |
| 2007/0027520 A1 | 2/2007 | Sherburne |
| 2007/0043430 A1 | 2/2007 | Stinson |
| 2007/0049903 A1 | 3/2007 | Jansen et al. |
| 2007/0078504 A1 | 4/2007 | Mialhe |
| 2007/0088323 A1 | 4/2007 | Campbell et al. |
| 2007/0100421 A1 | 5/2007 | Griffin |
| 2007/0117645 A1 | 5/2007 | Nakashima |
| 2007/0129706 A1 | 6/2007 | Katoh et al. |
| 2007/0149927 A1 | 6/2007 | Itou et al. |
| 2007/0161956 A1 | 7/2007 | Heuser |
| 2007/0185446 A1 | 8/2007 | Accisano |
| 2007/0203563 A1 | 8/2007 | Hebert et al. |
| 2007/0233224 A1 | 10/2007 | Leynov et al. |
| 2007/0239254 A1 | 10/2007 | Chia et al. |
| 2007/0239261 A1 | 10/2007 | Bose et al. |
| 2007/0250039 A1 | 10/2007 | Lobbins et al. |
| 2007/0250040 A1 | 10/2007 | Provost et al. |
| 2007/0255255 A1 | 11/2007 | Shah et al. |
| 2007/0255388 A1 | 11/2007 | Rudakov et al. |
| 2007/0270779 A1 | 11/2007 | Jacobs et al. |
| 2007/0299424 A1 | 12/2007 | Cumming et al. |
| 2007/0299500 A1 | 12/2007 | Hebert et al. |
| 2007/0299501 A1 | 12/2007 | Hebert et al. |
| 2007/0299502 A1 | 12/2007 | Hebert et al. |
| 2008/0009934 A1 | 1/2008 | Schneider et al. |
| 2008/0015558 A1 | 1/2008 | Harlan |
| 2008/0015678 A1 | 1/2008 | Kaplan et al. |
| 2008/0027528 A1 | 1/2008 | Jagger et al. |
| 2008/0033399 A1 | 2/2008 | Hunn et al. |
| 2008/0033528 A1 | 2/2008 | Satasiya et al. |
| 2008/0051705 A1 | 2/2008 | Von Oepen et al. |
| 2008/0051761 A1 | 2/2008 | Slazas et al. |
| 2008/0071301 A1 | 3/2008 | Matsuura et al. |
| 2008/0077229 A1 | 3/2008 | Andreas et al. |
| 2008/0082083 A1 | 4/2008 | Forde et al. |
| 2008/0091169 A1 | 4/2008 | Heideman et al. |
| 2008/0097398 A1 | 4/2008 | Mitelberg et al. |
| 2008/0108974 A1 | 5/2008 | Yee |
| 2008/0132933 A1 | 6/2008 | Gerber |
| 2008/0140180 A1 | 6/2008 | Dolan et al. |
| 2008/0147001 A1 | 6/2008 | Al-marashi et al. |
| 2008/0147162 A1 | 6/2008 | Andreas et al. |
| 2008/0177249 A1 | 7/2008 | Heuser et al. |
| 2008/0188865 A1 | 8/2008 | Miller et al. |
| 2008/0188928 A1 | 8/2008 | Salahieh et al. |
| 2008/0221666 A1 | 9/2008 | Licata et al. |
| 2008/0234660 A2 | 9/2008 | Cumming et al. |
| 2008/0234795 A1 | 9/2008 | Snow et al. |
| 2008/0243225 A1 | 10/2008 | Satasiya et al. |
| 2008/0255541 A1 | 10/2008 | Hoffman et al. |
| 2008/0255653 A1 | 10/2008 | Schkolnik |
| 2008/0255654 A1 | 10/2008 | Hebert et al. |
| 2008/0262471 A1 | 10/2008 | Warnock |
| 2008/0262472 A1 | 10/2008 | Lunn et al. |
| 2008/0262592 A1 | 10/2008 | Jordan et al. |
| 2008/0275426 A1 | 11/2008 | Holman et al. |
| 2008/0300667 A1 | 12/2008 | Hebert et al. |
| 2008/0312639 A1 | 12/2008 | Weber |
| 2009/0012500 A1 | 1/2009 | Murata et al. |
| 2009/0082609 A1 | 3/2009 | Condado |
| 2009/0105802 A1 | 4/2009 | Henry et al. |
| 2009/0125053 A1 | 5/2009 | Ferrera et al. |
| 2009/0132019 A1 | 5/2009 | Duffy et al. |
| 2009/0138066 A1 | 5/2009 | Leopold et al. |
| 2009/0143849 A1 | 6/2009 | Ozawa et al. |
| 2009/0149835 A1 | 6/2009 | Velasco et al. |
| 2009/0157048 A1 | 6/2009 | Sutermeister et al. |
| 2009/0160112 A1 | 6/2009 | Ostrovsky |
| 2009/0171319 A1 | 7/2009 | Guo et al. |
| 2009/0204196 A1 | 8/2009 | Weber |
| 2009/0240235 A1 | 9/2009 | Murata |
| 2009/0264985 A1 | 10/2009 | Bruszewski |
| 2009/0287182 A1 | 11/2009 | Bishop et al. |
| 2009/0287183 A1 | 11/2009 | Bishop et al. |
| 2009/0287187 A1 | 11/2009 | Legaspi et al. |
| 2009/0287292 A1 | 11/2009 | Becking et al. |
| 2009/0299333 A1 | 12/2009 | Wendlandt et al. |
| 2009/0299449 A1 | 12/2009 | Styrc |
| 2009/0318947 A1 | 12/2009 | Garcia et al. |
| 2010/0020354 A1 | 1/2010 | Ito |
| 2010/0036363 A1 | 2/2010 | Watanabe et al. |
| 2010/0049293 A1 | 2/2010 | Zukowski et al. |
| 2010/0049297 A1 | 2/2010 | Dorn |
| 2010/0057184 A1 | 3/2010 | Randolph et al. |
| 2010/0057185 A1 | 3/2010 | Melsheimer et al. |
| 2010/0069852 A1 | 3/2010 | Kelley |
| 2010/0087913 A1 | 4/2010 | Rabkin et al. |
| 2010/0094258 A1 | 4/2010 | Shimogami et al. |
| 2010/0094394 A1 | 4/2010 | Beach et al. |
| 2010/0094395 A1 | 4/2010 | Kellett |
| 2010/0100106 A1 | 4/2010 | Ferrera |
| 2010/0160863 A1 | 6/2010 | Heuser |
| 2010/0198334 A1 | 8/2010 | Yodfat et al. |
| 2010/0204770 A1 | 8/2010 | Mas et al. |
| 2010/0217235 A1 | 8/2010 | Thorstenson et al. |
| 2010/0256602 A1 | 10/2010 | Lippert et al. |
| 2010/0256603 A1 | 10/2010 | Lippert et al. |
| 2010/0262157 A1 | 10/2010 | Silver et al. |
| 2010/0268243 A1 | 10/2010 | Parker |
| 2010/0268328 A1 | 10/2010 | Stiger |
| 2010/0274270 A1 | 10/2010 | Patel et al. |
| 2010/0298931 A1 | 11/2010 | Quadri et al. |
| 2010/0331951 A1 | 12/2010 | Bei et al. |

(56) References Cited

U.S. PATENT DOCUMENTS

| | | |
|---|---|---|
| 2011/0009943 A1 | 1/2011 | Paul et al. |
| 2011/0022157 A1 | 1/2011 | Essinger et al. |
| 2011/0029065 A1 | 2/2011 | Wood et al. |
| 2011/0034987 A1 | 2/2011 | Kennedy |
| 2011/0054586 A1 | 3/2011 | Mayberry et al. |
| 2011/0093055 A1 | 4/2011 | Kujawski |
| 2011/0098804 A1 | 4/2011 | Yeung et al. |
| 2011/0106235 A1 | 5/2011 | Haverkost et al. |
| 2011/0112623 A1 | 5/2011 | Schatz |
| 2011/0137403 A1 | 6/2011 | Rasmussen et al. |
| 2011/0152760 A1 | 6/2011 | Parker |
| 2011/0160763 A1 | 6/2011 | Ferrera et al. |
| 2011/0178588 A1 | 7/2011 | Haselby |
| 2011/0190862 A1 | 8/2011 | Bashiri et al. |
| 2011/0190865 A1 | 8/2011 | Mchugo et al. |
| 2011/0208292 A1 | 8/2011 | Von Oepen et al. |
| 2011/0224650 A1 | 9/2011 | Itou et al. |
| 2011/0257720 A1 | 10/2011 | Peterson et al. |
| 2011/0288626 A1 | 11/2011 | Straubinger et al. |
| 2011/0319904 A1 | 12/2011 | Hollett et al. |
| 2012/0029607 A1 | 2/2012 | Mchugo et al. |
| 2012/0035700 A1 | 2/2012 | Leanna et al. |
| 2012/0053681 A1 | 3/2012 | Alkhatib et al. |
| 2012/0059449 A1 | 3/2012 | Dorn et al. |
| 2012/0065660 A1 | 3/2012 | Ferrera et al. |
| 2012/0116494 A1 | 5/2012 | Leynov et al. |
| 2012/0123511 A1 | 5/2012 | Brown |
| 2012/0226343 A1 | 9/2012 | Vo et al. |
| 2012/0253447 A1 | 10/2012 | Hayasaka et al. |
| 2012/0316638 A1 | 12/2012 | Grad et al. |
| 2013/0085562 A1 | 4/2013 | Rincon et al. |
| 2013/0131775 A1 | 5/2013 | Hadley et al. |
| 2013/0172925 A1 | 7/2013 | Garcia et al. |
| 2013/0172979 A1 | 7/2013 | Fargahi |
| 2013/0226276 A1 | 8/2013 | Newell et al. |
| 2013/0226278 A1 | 8/2013 | Newell et al. |
| 2013/0261730 A1 | 10/2013 | Bose et al. |
| 2013/0274618 A1 | 10/2013 | Hou et al. |
| 2013/0274859 A1 | 10/2013 | Argentine |
| 2013/0282099 A1 | 10/2013 | Huynh |
| 2013/0304185 A1 | 11/2013 | Newell et al. |
| 2014/0025150 A1 | 1/2014 | Lim |
| 2014/0031918 A1 | 1/2014 | Newell et al. |
| 2014/0148893 A1 | 5/2014 | Kusleika |
| 2014/0171826 A1 | 6/2014 | Lampropoulos et al. |
| 2014/0172067 A1 | 6/2014 | Brown et al. |
| 2014/0194919 A1 | 7/2014 | Losordo et al. |
| 2014/0200648 A1 | 7/2014 | Newell et al. |
| 2014/0277332 A1 | 9/2014 | Slazas et al. |
| 2015/0032198 A1 | 1/2015 | Folk |
| 2015/0066128 A1 | 3/2015 | Losordo et al. |
| 2015/0066129 A1 | 3/2015 | Nageswaran et al. |
| 2015/0066130 A1 | 3/2015 | Haggstrom et al. |
| 2015/0066131 A1 | 3/2015 | Luong et al. |
| 2015/0080937 A1 | 3/2015 | Davidson |
| 2015/0133990 A1 | 5/2015 | Davidson |
| 2015/0164666 A1 | 6/2015 | Johnson et al. |
| 2015/0238336 A1 | 8/2015 | Johnson et al. |
| 2016/0113793 A1 | 4/2016 | Nishigishi |
| 2017/0035592 A1 | 2/2017 | Haggstrom et al. |
| 2018/0200092 A1 | 7/2018 | Nageswaran et al. |
| 2018/0263799 A1 | 9/2018 | Elwood et al. |
| 2019/0314175 A1 | 10/2019 | Dawson et al. |
| 2019/0314176 A1 | 10/2019 | Nageswaran et al. |
| 2019/0314177 A1 | 10/2019 | Alonso et al. |
| 2019/0314179 A1 | 10/2019 | Nageswaran et al. |

FOREIGN PATENT DOCUMENTS

| | | |
|---|---|---|
| JP | 2001504016 A | 3/2001 |
| JP | 2008518717 A | 6/2008 |
| JP | 2009542357 A | 12/2009 |
| JP | 2013500777 A | 1/2013 |
| JP | 2013158647 A | 8/2013 |
| WO | WO 9820811 A1 | 5/1998 |
| WO | WO 2010127838 A2 | 11/2010 |
| WO | WO 2011076408 A1 | 6/2011 |
| WO | WO 2011081997 A1 | 7/2011 |
| WO | 2011122444 A1 | 10/2011 |
| WO | WO 2012158152 A1 | 11/2012 |
| WO | 2014074462 A2 | 5/2014 |

COUPLING UNITS FOR MEDICAL DEVICE DELIVERY SYSTEMS

CROSS-REFERENCE TO RELATED APPLICATION(S)

The present application claims the benefit of U.S. patent application Ser. No. 15/410,444, filed Jan. 19, 2017, which is incorporated herein by reference in its entirety.

BACKGROUND

Walls of the vasculature, particularly arterial walls, may develop areas of pathological dilatation called aneurysms that often have thin, weak walls that are prone to rupturing. Aneurysms are generally caused by weakening of the vessel wall due to disease, injury, or a congenital abnormality. Aneurysms occur in different parts of the body, and the most common are abdominal aortic aneurysms and cerebral (e.g., brain) aneurysms in the neurovasculature. When the weakened wall of an aneurysm ruptures, it can result in death, especially if it is a cerebral aneurysm that ruptures.

Aneurysms are generally treated by excluding or at least partially isolating the weakened part of the vessel from the arterial circulation. For example, conventional aneurysm treatments include: (i) surgical clipping, where a metal clip is secured around the base of the aneurysm; (ii) packing the aneurysm with small, flexible wire coils (micro-coils); (iii) using embolic materials to "fill" an aneurysm; (iv) using detachable balloons or coils to occlude the parent vessel that supplies the aneurysm; and (v) intravascular stenting.

Intravascular stents are well known in the medical arts for the treatment of vascular stenoses or aneurysms. Stents are prostheses that expand radially or otherwise within a vessel or lumen to support the vessel from collapsing. Methods for delivering these intravascular stents are also well known.

Conventional methods of introducing a compressed stent into a vessel and positioning it within an area of stenosis or an aneurysm include percutaneously advancing a distal portion of a guiding catheter through the vascular system of a patient until the distal portion is proximate the stenosis or aneurysm. A second, inner catheter and a guidewire within the inner catheter are advanced through the distal region of the guiding catheter. The guidewire is then advanced out of the distal region of the guiding catheter into the vessel until the distal portion of the guidewire carrying the compressed stent is positioned at the point of the lesion within the vessel. The compressed stent is then released and expanded so that it supports the vessel at the point of the lesion.

SUMMARY

The present technology is illustrated, for example, according to various aspects described below. Various examples of aspects of the present technology are described as numbered clauses (1, 2, 3, etc.) for convenience. These are provided as examples and do not limit the present technology. It is noted that any of the dependent clauses may be combined in any combination, and placed into a respective independent clause, e.g., Clause 1 or Clause 23. The other clauses can be presented in a similar manner.

1. A stent delivery system, comprising:
 a core member having a distal segment;
 a coupler positioned about the core member distal segment and rotatably coupled to the core member, the coupler comprising a rigid plate having a first end surface, a second end surface, and a side surface extending between the first and second end surfaces, the side surface comprising one or more projections separated by recesses; and
 a stent extending along the core member distal segment such that an inner surface of the stent is engaged by the one or more projections of the coupler.

2. The stent delivery system of Clause 1, wherein the projections comprise rounded edges.

3. The stent delivery system of Clause 1, wherein the one or more projections comprises three or more projections.

4. The stent delivery system of Clause 1, wherein a longest dimension of the first and second end surfaces is configured to fit within a 0.017", 0.021" or 0.027" inner diameter catheter.

5. The stent delivery system of Clause 1, wherein a maximum length of the first and second end surfaces is at least 5 times greater than a length of the side surface, the maximum length of the first and second end surfaces being generally orthogonal to the length of the side surface.

6. The stent delivery system of Clause 1, wherein the rigid plate comprises at least one of a metal or a rigid polymer.

7. The stent delivery system of Clause 1, wherein the rigid plate side surface has a length of between about 25-100 microns.

8. The stent delivery system of Clause 1, wherein the rigid plate is a first rigid plate, the stent delivery system further comprising:
 a second rigid plate positioned about the core member distal segment and spaced apart from the first rigid plate; and
 a spacer positioned about the core member distal segment, the spacer positioned between the first rigid plate and the second rigid plate.

9. The stent delivery system of Clause 8, wherein the spacer comprises a cylindrical body having end walls orthogonal to a long axis of the core member.

10. The stent delivery system of Clause 8, wherein the first and second rigid plates are spaced apart from one another by a distance corresponding to a pore pitch of the stent.

11. The stent delivery system of Clause 1, wherein the first and second end surfaces are substantially orthogonal to a long axis of the core member.

12. The stent delivery system of Clause 1, wherein the projections interlock with the stent such that each projection is at least partially received within a pore of the stent.

13. A stent delivery system, comprising:
 a catheter having a lumen and an inner surface extending along the lumen;
 a core member, extending within the catheter lumen;
 a plate comprising:
  a first end surface, a second end surface, and a side surface extending between the first end surface and the second end surface; and
  an aperture extending through the first and second end surfaces, the core member extending through the aperture such that the plate can rotate about the core member; and
 a stent extending along the core member and over the plate, at least a portion of the stent being radially positioned between the plate side surface and the catheter inner surface.

14. The stent delivery system of Clause 13, wherein the plate side surface comprises a plurality of projections separated by recesses.

15. The stent delivery system of Clause 14, wherein the projections interlock with the stent such that each projection is at least partially received within a pore of the stent.

16. The stent delivery system of Clause 14, wherein the one or more projections comprises three or more projections.

17. The stent delivery system of Clause 13, wherein a maximum length of the first and second end surfaces is at least 5 times greater than a length of the side surface, the maximum length of the first and second end surfaces being generally orthogonal to the length of the side surface.

18. The stent delivery system of Clause 13, wherein the plate comprises at least one of a metal or a rigid polymer.

19. The stent delivery system of Clause 13, wherein the plate is a first plate, the stent delivery system further comprising:

a second plate positioned about the core member and spaced apart from the first plate; and a spacer positioned about the core member and positioned between the first plate and the second plate.

20. The stent delivery system of Clause 19, wherein the spacer comprises a cylindrical body having end walls orthogonal to a long axis of the core member.

21. The stent delivery system of Clause 19, wherein the first and second plates are spaced apart from one another by a distance corresponding to a pore pitch of the stent.

22. A core assembly comprising:

a core member;

a first rigid plate around the core member;

a second rigid plate around the core member and spaced apart from the first rigid plate; and a spacer around the core member, the spacer disposed between the first rigid plate and the second rigid plate.

23. The core member of Clause 22, wherein the first and second rigid plates each comprise:

a first end surface;

a second end surface opposite the first end surface;

a side surface extending between the first and second end surfaces, the side surface comprising a plurality of projections separated by recesses; and an aperture extending through the first and second end surfaces, the aperture receiving the core member therethrough.

24. The core member of Clause 23, wherein the one or more projections comprises three or more projections.

25. The core member of Clause 23, wherein a maximum length of the first and second end surfaces is at least 5 times greater than a length of the side surface, the maximum length of the first and second end surfaces being generally orthogonal to the length of the side surface.

26. The core member of Clause 23, wherein the first and second end surfaces are substantially orthogonal to a long axis of the core member.

27. The core member of Clause 22, wherein the first and second rigid plates comprise at least one of a metal or a rigid polymer.

28. The core member of Clause 22, wherein the first and second rigid plates each have a thickness of between about 25-100 microns.

29. The core member of Clause 22, wherein the spacer comprises a cylindrical body having end walls orthogonal to a long axis of the core member.

30. A rigid plate for engaging a stent, the plate comprising:

first and second end surfaces;

a side surface extending between the first and second end surfaces, the side surface including a plurality of projections separated by recesses; and a central opening extending through the rigid plate between the first and second end surfaces.

31. The rigid plate of Clause 30, wherein the projections comprise rounded edges.

32. The rigid plate of Clause 30, wherein the one or more projections comprises three or more projections.

33. The rigid plate of Clause 30, wherein a longest dimension of the first and second end surfaces is configured to fit within a 0.017", 0.021" or 0.027" inner diameter catheter.

34. The rigid plate of Clause 30, wherein a maximum length of the first and second end surfaces is at least 5 times greater than a length of the side surface, the maximum length of the first and second end surfaces being generally orthogonal to the length of the side surface.

35. The rigid plate of Clause 30, wherein the rigid plate comprises at least one of a metal or a rigid polymer.

36. The rigid plate of Clause 30, wherein the side surface has a length of between about 25-100 microns.

37. The rigid plate of Clause 30, wherein the first and second end surfaces are substantially orthogonal to a long axis of the central opening.

Additional features and advantages of the present technology will be set forth in the description below, and in part will be apparent from the description, or may be learned by practice of the subject technology. The advantages of the present technology will be realized and attained by the structure particularly pointed out in the written description and claims hereof as well as the appended drawings.

It is to be understood that both the foregoing general description and the following detailed description are exemplary and explanatory and are intended to provide further explanation of the present technology as claimed.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present technology. For ease of reference, throughout this disclosure identical reference numbers may be used to identify identical or at least generally similar or analogous components or features.

DETAILED DESCRIPTION

Figure 1:
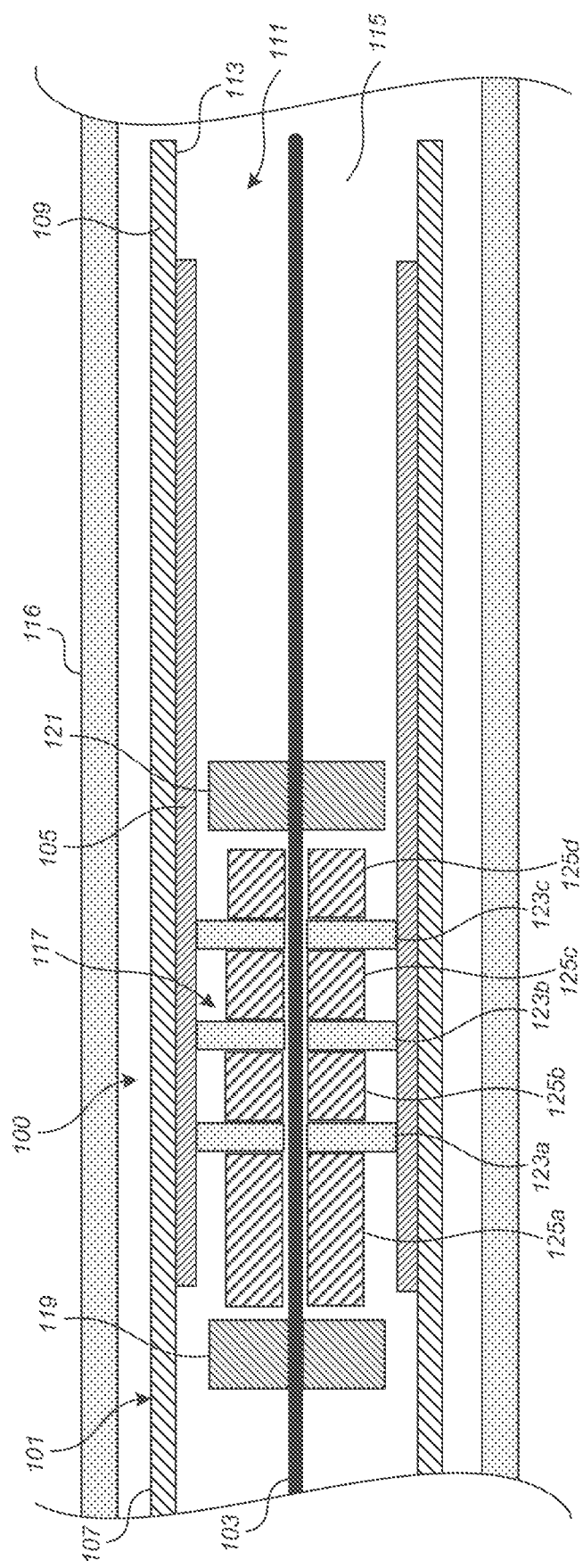
FIG. 1 is a schematic illustration of a medical device delivery system configured in accordance with some embodiments.

Conventional stent couplers include soft "pads" that rely on friction fit to secure a stent (such as a braided, knit or woven stent) against an inner wall of a catheter. Such friction-fit pads may require several different pad diameters to accommodate different stent wire size mixes. That is, within a given catheter size, the internal diameter of the compressed (braided, knit or woven) stent contained in the catheter will vary based on the sizes (diameters) of the wires, and possibly other parameters of the stent corresponding to different deployed sizes or target vessel sizes. This can require using different pad diameters to accommodate different stent sizes within a desired range (e.g. about 3.5 to 5 millimeters in diameter), which necessitates manufacturing the pads of various diameters to very small size tolerances. Embodiments of the present technology can allow a single size coupler to be used with a relatively broad range of stent inner diameters within a given catheter size (e.g. a 0.027", 0.021", or 0.017" inner diameter catheter). For example, a coupler comprising a rigid plate that has a plurality of projections separated by recesses can be used to secure a range of different stent sizes within a given catheter.

Specific details of several embodiments of the present technology are described herein with reference to FIGS. 1-7. Although many of the embodiments are described with respect to devices, systems, and methods for delivery of stents and other medical devices, other applications and other embodiments in addition to those described herein are within the scope of the present technology. It should be noted that other embodiments in addition to those disclosed herein are within the scope of the present technology. Further, embodiments of the present technology can have different configurations, components, and/or procedures than those shown or described herein. Moreover, embodiments of the present technology can have configurations, components, and/or procedures in addition to those shown or described herein and that these and other embodiments may not have several of the configurations, components, and/or procedures shown or described herein without deviating from the present technology.

As used herein, the terms "distal" and "proximal" define a position or direction with respect to a clinician or a clinician's control device (e.g., a handle of a delivery catheter). For example, the terms, "distal" and "distally" refer to a position distant from or in a direction away from a clinician or a clinician's control device along the length of device. In a related example, the terms "proximal" and "proximally" refer to a position near or in a direction toward a clinician or a clinician's control device along the length of device. The headings provided herein are for convenience only and should not be construed as limiting the subject matter disclosed.

Selected Examples of Couplers for Medical Device Delivery Systems

FIGS. 1-7 depict embodiments of medical device delivery systems that may be used to deliver and/or deploy a medical device, such as but not limited to a stent, into a hollow anatomical structure such as a blood vessel. The stent can comprise a braided stent or other form of stent such as a woven stent, knit stent, laser-cut stent, roll-up stent, etc. The stent can optionally be configured to act as a "flow diverter" device for treatment of aneurysms, such as those found in blood vessels including arteries in the brain or within the cranium, or in other locations in the body such as peripheral arteries. The stent can optionally be similar to any of the versions or sizes of the PIPELINE™ Embolization Device marketed by Medtronic Neurovascular of Irvine, Calif. USA. The stent can alternatively comprise any suitable tubular medical device and/or other features, as described herein.

FIG. 1 is a schematic illustration of a medical device delivery system 100 configured in accordance with an embodiment of the present technology. The system 100 can comprise an elongate tube or catheter 101 which slidably receives a core member 103 configured to carry a stent 105 through the catheter 101. The depicted catheter 101 has a proximal region 107 and an opposing distal region 109 which can be positioned at a treatment site within a patient, an internal lumen 111 extending from the proximal region 107 to the distal region 109, and an inner surface 113 defining the lumen 111. At the distal region 109, the catheter 101 has a distal opening 115 through which the core member 103 may be advanced beyond the distal region 109 to expand or deploy the stent 105 within the blood vessel 116. The proximal region 107 may include a catheter hub (not shown). The catheter 101 can define a generally longitudinal dimension extending between the proximal region 107 and the distal region 109. When the delivery system 100 is in use, the longitudinal dimension need not be straight along some or any of its length.

The core member 103 is configured to extend generally longitudinally through the lumen 111 of the catheter 101. The core member 103 can generally comprise any member(s) with sufficient flexibility and column strength to move the stent 105 or other medical device through the catheter 101. The core member 103 can therefore comprise a wire, tube (e.g., hypotube), braid, coil, or other suitable member(s), or a combination of wire(s), tube(s), braid(s), coil(s), etc.

The system 100 can also include a coupling unit 117 (e.g., a device interface) configured to releasably retain the medical device or stent 105 with respect to the core member 103. The coupling unit 117 is configured to underlie and engage an inner wall of the stent 105. In this manner, the coupling unit 117 cooperates with the overlying inner surface 113 of the catheter 101 to grip the stent 105 such that the coupling unit 117 can move the stent 105 along and within the catheter 101, e.g., distal and/or proximal movement of the core member 103 relative to the catheter 101 results in a corresponding distal and/or proximal movement of the stent 105 within the catheter lumen 111.

The coupling unit 117 can, in some embodiments, be configured to rotate about the core member 103. In some such embodiments, the coupling unit 117 can comprise a proximal restraint 119 and a distal restraint 121. The proximal and distal restraints 119, 121 can be fixed to the core member 103 to prevent or limit proximal or distal movement of the coupling unit 117 along the longitudinal dimension of the core member 103. One or both of the proximal and distal restraints 119, 121 can have an outside diameter or other radially outermost dimension that is smaller than the outside diameter or other radially outermost dimension of the coupling unit 117 such that one or both of the restraints 119, 121 do not contact the inner surface of the stent 105.

The coupling unit 117 can also include one or more couplers 123a-c (e.g., stent engagement members) disposed about the core member 103 and between the proximal and distal restraints 119, 121 and spacer(s) 125a-d. In the illustrated embodiment, the couplers 123a-c are spaced apart from each other by spacers 125b-c, the coupler 123a is spaced apart from the proximal restraint 119 by spacer 125a, and the coupler 123c is spaced apart from the distal restraint by spacer 125d (which can be omitted in some embodiments of the coupling unit 117). One, some or all of the couplers 123a-c can be a rigid plate with a central aperture configured to receive the core member 103 therethrough. The couplers 123a-c are configured to mechanically engage the stent 105 such that the couplers 123a-c retain the stent 105 from moving longitudinally with respect to the core member 103. The spacers 125a-d can each be a substantially cylindrical body with an aperture configured to receive the core member 103 therethrough. One or all of the spacers 125a-d can have an outside diameter or other radially outermost dimension that is smaller than the outside diameter or other radially outermost dimension of the couplers 123a-c so the spacers 125a-d do not contact the inner surface of the stent 105.

Although the embodiment illustrated in FIG. 1 includes three couplers 123a-c and four spacers 125a-d, the number of couplers and spacers can vary. In at least one embodiment, the coupling unit 117 includes only a single coupler without any spacers. In other embodiments, the number of couplers can vary, for example two, three, four, five, six, or more couplers separated by spacers.

In operation, the stent 105 can be moved distally or proximally within the catheter 101 via the core member 103 and the coupling unit 117. To move the stent 105 out of the catheter 101, either the core member 103 is moved distally while the catheter 101 is held stationary or the core member 103 is held stationary while the catheter 101 is withdrawn proximally. When the core member 103 is moved distally and the catheter 101 is held stationary, the proximal restraint 119 bears against the proximal-most spacer 125a and causes the spacers 125a-d and the couplers 123a-c to be advanced distally. The mechanical engagement between the couplers 123a-c and the stent 105 causes the stent 105 to move distally with the couplers 123a-c to deploy the stent 105 out of the distal region 109 of the catheter 101. Conversely, to recapture or otherwise move the stent 105 into the catheter 101, the relative movement between the core member 103 and the catheter 101 is reversed compared moving the stent 105 out of the catheter such that the proximal region of the distal restraint 121 bears against the distal region of the distal-most spacer 125d and thereby causes the spacers 125a-d and the couplers 123a-c to be retracted relative to the catheter 101. The mechanical engagement between the couplers 123a-c and the stent 105 accordingly holds the stent 105 with respect to the core member 103 such that proximal movement of the stent 105 relative to the catheter 101 enables re-sheathing of the stent 105 back into the distal region 109 of the catheter 101. This is useful when the stent 105 has been partially deployed and a portion of the stent remains disposed between at least one of the couplers 123a-c (e.g. the proximal-most coupler 123a) and the inner surface 113 of the catheter 101 because the stent 105 can be withdrawn back into the distal opening 115 of the catheter 101 by moving the core member 103 proximally relative to the catheter 101 (and/or moving the catheter 101 distally relative to the core member 103). Re-sheathing in this manner remains possible until the couplers 123a-c and/or catheter 101 have been moved to a point where the proximal-most coupler 123a is beyond the distal opening 115 of the catheter 101 and the stent 105 is released from between the member 123a and the catheter 101.

The couplers 123a-c and the spacers 125a-d can be fixed to the core member 103 so as to be immovable relative to the core member 103, either in a longitudinal/sliding manner or a radial/rotational manner. Alternatively, the spacers 125a-d and/or the couplers 123a-c can be coupled to (e.g., mounted on) the core member 103 so that the spacers 125a-d and/or the couplers 123a-c can rotate about the longitudinal axis of the core member 103, and/or move or slide longitudinally along the core member 103. In such embodiments, the spacers 125a-d and/or the couplers 123a-c can each have an inner lumen or aperture that receives the core member 103 therein such that the spacers 125a-d and/or the couplers 123a-c can slide and/or rotate relative to the core member 103. Additionally in such embodiments, the proximal and distal restraints 119, 121 can be spaced apart along the core member 103 by a longitudinal distance that is slightly greater than the combined length of the spacers 125a-d and the couplers 123a-c, so as to leave one or more longitudinal gaps between the proximal-most and distal-most spacers 125a, 125d, respectively, and the proximal and distal restraints 119, 121. When present, the longitudinal gap(s) allow the spacers 125a-d and the couplers 123a-c to slide longitudinally along the core member 103 between the restraints 119, 121. The longitudinal range of motion of the spacers 125a-d and the couplers 123a-c between the restraints 119, 121 is approximately equal to the total combined length of the longitudinal gap(s).

Instead of or in addition to the longitudinal gap(s), the coupling unit 117 can include radial gaps between the outer surface of the core member 103 and the inner surface of the spacers 125a-d and the couplers 123a-c. Such radial gaps can be formed when the spacers 125a-d and/or the couplers 123a-c are constructed with holes that are somewhat larger than the outer diameter of the corresponding portion of the core member 103. When present, the radial gaps allow the spacers 125a-d and/or the couplers 123a-c to rotate about the longitudinal axis of the core member 103 between the restraints 119, 121. The presence of longitudinal gaps of at least a minimal size on either side of the spacers 125a-d and the couplers 123a-c can also facilitate the rotatability of the spacers 125a-d and the couplers 123a-c.

Figure 2:
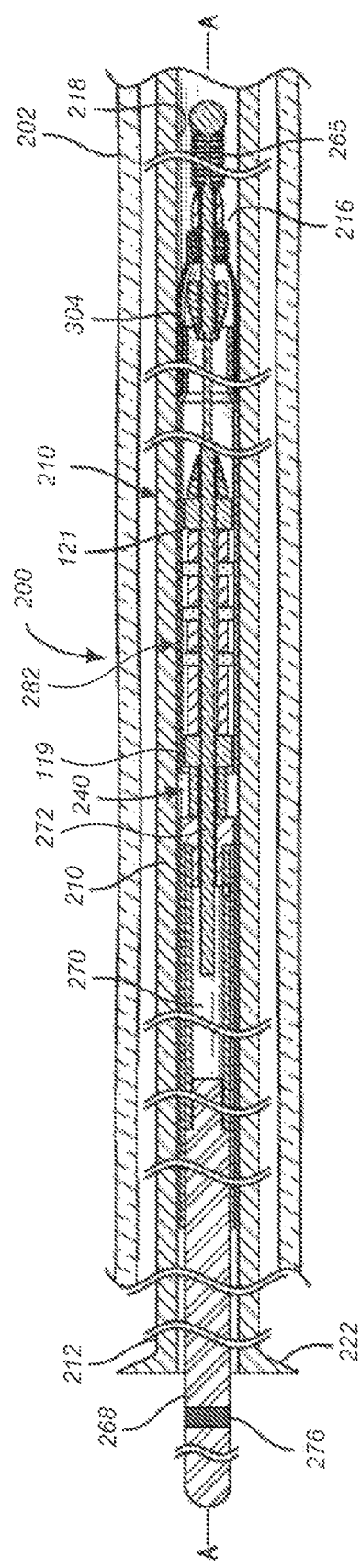
FIG. 2 is a side, cross-sectional view of a medical device delivery system disposed within a body lumen, according to some embodiments.
Figure 3:
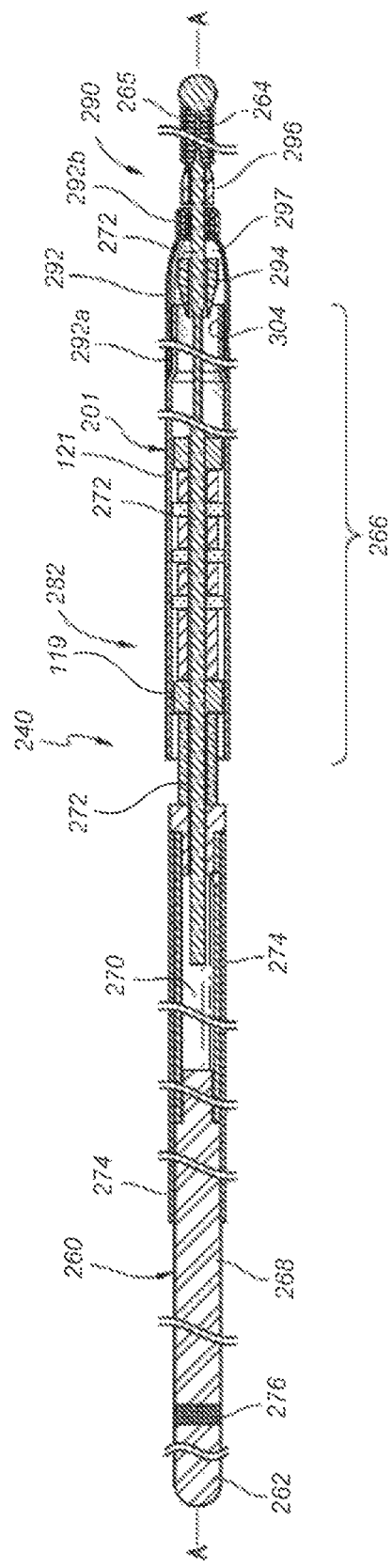
FIG. 3 is a side, cross-sectional view of a core assembly of the medical device delivery system shown in FIG. 2, according to some embodiments.
Figure 4:
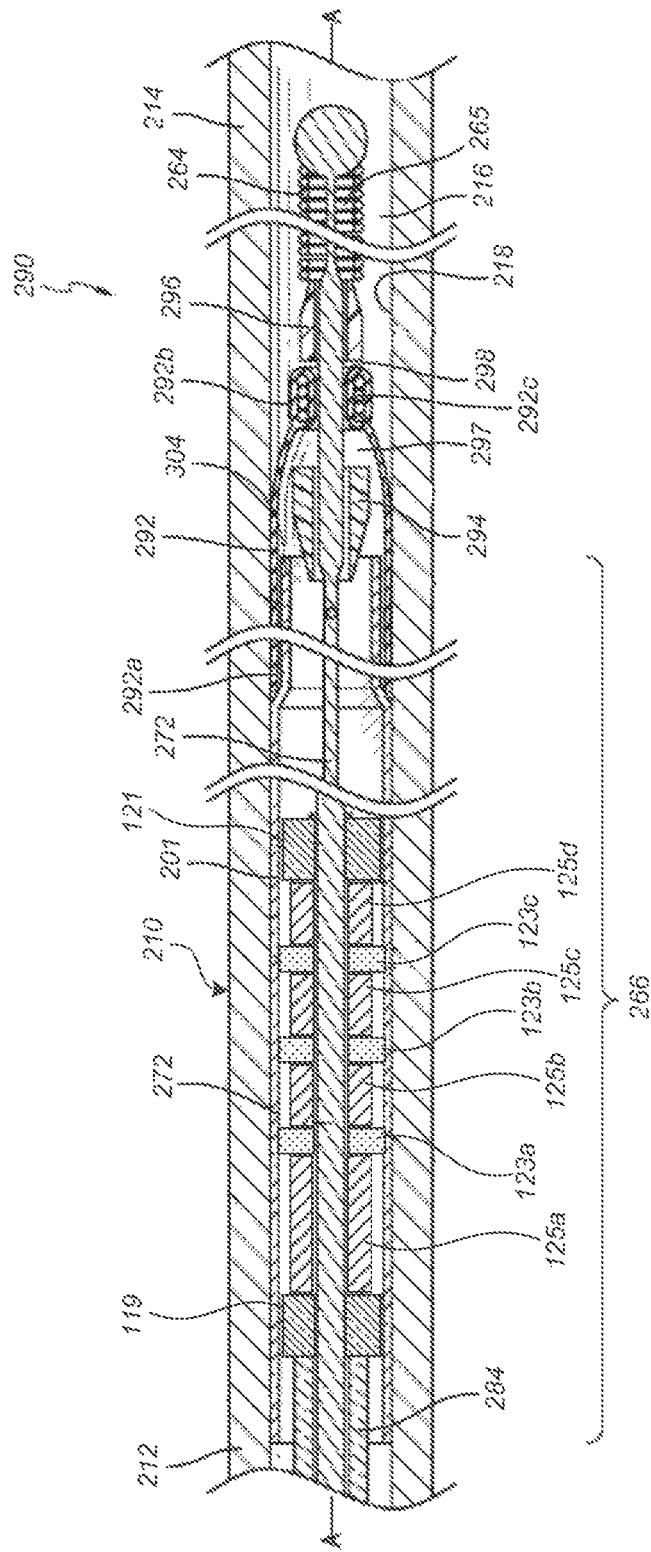
FIG. 4 is an enlarged side, cross-sectional view of the delivery system shown in FIG. 2.

FIGS. 2-4 illustrate another embodiment of a medical device delivery system configured in accordance with an embodiment of the present technology. As shown in FIG. 2, the depicted medical device delivery system 200 can comprise an elongate tube or catheter 210 which slidably receives a core assembly 240 configured to carry the stent 201 through the catheter 210. FIG. 3 illustrates the core assembly 240 without depicting the catheter 210 and blood vessel 202 for clarity. The depicted catheter 210 (see FIGS. 2 and 4) has a proximal region 212 and an opposing distal region 214 which can be positioned at a treatment site within a patient, an internal lumen 216 extending from the proximal region 212 to the distal region 214, and an inner surface 218 facing the lumen 216. At the distal region 214, the catheter 210 has a distal opening (not shown) through which the core assembly 240 may be advanced beyond the distal region 214 to expand or deploy the stent 201 within the blood vessel 202. The proximal region 212 may include a catheter hub 222. The catheter 210 can define a generally longitudinal dimension A-A extending between the proximal region 212 and the distal region 214. When the delivery system 200 is in use, the longitudinal dimension need not be straight along some or any of its length.

The catheter 101/210 can optionally comprise a microcatheter. For example, the catheter 101/210 can optionally comprise any of the various lengths of the MARKSMAN™ catheter available from Medtronic Neurovascular of Irvine, Calif. USA. The catheter 101/210 can optionally comprise a microcatheter having an inner diameter of about 0.030 inches or less, and/or an outer diameter of 3 French or less near the distal region 109/214. Instead of or in addition to these specifications, the catheter 101/210 can comprise a microcatheter which is configured to percutaneously access the internal carotid artery, or another location within the neurovasculature distal of the internal carotid artery, with its distal opening 113.

The core assembly 240 can comprise a core member 260 configured to extend generally longitudinally through the lumen 216 of the catheter 210. The core member 260 can have a proximal region or section 262 and a terminal or distal region 264, which can optionally include a tip coil 265. The core member 260 can also comprise an intermediate portion 266 located between the proximal region 262 and the distal region 264, which intermediate portion is the portion of the core member 260 onto or over which the stent 201 is positioned or fitted or extends when the core assembly 240 is in the pre-deployment configuration as shown in FIGS. 2-4.

The core member 260 can generally comprise any member(s) with sufficient flexibility and column strength to move the stent 201 or other medical device through the catheter 210. The core member 260 can therefore comprise a wire, tube (e.g., hypotube), braid, coil, or other suitable member(s), or a combination of wire(s), tube(s), braid(s), coil(s), etc. The embodiment of the core member 260 depicted in FIGS. 2-4 is of multi-member construction, comprising a proximal wire 268, a tube 270 (e.g., a hypotube) connected at its proximal region to a distal region of the proximal wire 268, and a distal wire 272 connected at its proximal region to a distal region of the tube 270. An outer layer 274, which can comprise a layer of lubricious material such as PTFE (polytetrafluoroethylene or TEFLON™) or other lubricious polymers, can cover some or all of the tube 270 and/or proximal wire 268. The proximal and/or distal wires 268, 272 may taper or vary in diameter along some or all of their lengths. The proximal wire 268 may include one or more fluorosafe markers 276, and such marker(s) can be located on a portion of the wire 268 that is not covered by the outer layer 274 (e.g., proximal of the outer layer 274). This portion of the wire 268 marked by the marker(s) 276, and/or proximal of any outer layer 274, can comprise a bare metal outer surface.

The core assembly 240 can further comprise a proximal coupling unit 282 and/or a distal coupling unit 290 that can interconnect the medical device or stent 201 with the core member 260. The proximal coupling unit 282 can comprise one or more couplers 123a-c that are configured to underlie the stent 201 and engage an inner wall of the stent. In this manner, the proximal coupling unit 282 cooperates with the overlying inner surface 218 of the catheter 210 to grip the stent 201 such that the proximal coupling unit 282 can move the stent 201 along and within the catheter 210, e.g., as the user pushes the core member 260 distally and/or pulls the core member proximally relative to the catheter 210, resulting in a corresponding distal and/or proximal movement of the stent 201 within the catheter lumen 216.

The proximal coupling unit 282 can, in some embodiments, be similar to any of the versions or embodiments of the coupling unit 117 described above with respect to FIG. 1. For example, the proximal coupling unit 282 can include proximal and distal restraints 119, 121 that are fixed to the core member 260 (e.g., to the distal wire 272 thereof in the depicted embodiment) so as to be immovable relative to the core member 260, either in a longitudinal/sliding manner or a radial/rotational manner. The proximal coupling unit 282 can also include a plurality of couplers 123a-c separated by spacers 125a-d. The couplers 123a-c and spacers 125a-d can be coupled to (e.g., mounted on) the core member 260 so that the proximal coupling unit 282 can rotate about the longitudinal axis A-A of the core member 260 (e.g., of the distal wire 272), and/or move or slide longitudinally along the core member. One or both of the proximal and distal restraints 119, 121 can have an outside diameter or other radially outermost dimension that is smaller than the outside diameter or other radially outermost dimension of the proximal coupling unit 282, so that one or both of the restraints 119, 121 will tend not to contact the inner surface of the stent 201 during operation of the core assembly 240.

In the proximal coupling unit 282 shown in FIGS. 2-4, the stent 201 can be moved distally or proximally within the catheter 210 via the proximal coupling unit 282 and in some embodiments the stent 201 can be resheathed via the proximal coupling unit 282 after partial deployment from the distal opening of the catheter 210, in a manner similar to that described above with respect to the coupling unit 117 in FIG. 1.

Optionally, the proximal edge of the proximal coupling unit 282 can be positioned just distal of the proximal edge of the stent 201 when in the delivery configuration shown in FIGS. 2-4. In some such embodiments, this enables the stent 201 to be re-sheathed when as little as a few millimeters of the stent remains in the catheter 210. Therefore, with stents 201 of typical length, resheathability of 75% or more can be provided (i.e. the stent 201 can be re-sheathed when 75% or more of it has been deployed).

The distal coupling unit 290 can comprise a distal engagement member 292 that can take the form of, for example, a distal device cover or distal stent cover (generically, a "distal cover"). The distal cover 292 can be configured to reduce friction between the medical device or stent 201 (e.g., the distal portion or distal region thereof) and the inner surface 218 of the catheter 210. For example, the distal cover 292 can be configured as a lubricious, flexible structure having a free first end or section 292a that can extend over at least a portion of the stent 201 and/or intermediate portion 266 of the core member 260, and a fixed second end or section 292b that can be coupled (directly or indirectly) to the core member 260.

The distal cover 292 can have a first or delivery position, configuration, or orientation in which the distal cover can extend proximally relative to the distal tip 264, or proximally from the second section 292b or its (direct or indirect) attachment to the core member 260, and at least partially surround or cover a distal portion of the stent 201. The distal cover 292 can be movable from the first or delivery orientation to a second or resheathing position, configuration, or orientation (not shown) in which the distal cover can be everted such that the first end 292a of the distal cover is positioned distally relative to the second end 292b of the distal cover 292 to enable the resheathing of the core assembly 240, either with the stent 201 carried thereby, or without the stent.

The distal cover 292, particularly the first end 292a thereof, can comprise one or more flexible, generally longitudinally extending strips, wings, or elongate portions that are coupled to or integrally formed with the second end 292b. The distal cover 292 can be manufactured or otherwise cut from a tube of the material selected for the distal cover or from multiple radial portions of such a tube. In such embodiments the first section 292a may be formed as multiple longitudinal strips cut from the tube, and the second section 292b may be an uncut (or similarly cut) length of the tube. Accordingly, the second section 292b and the proximally extending strips of the first section 292a may form a single, integral device or structure. In some embodiments, the distal cover 292 comprises only one, or no more than two strips, wings, or elongate portions.

In some embodiments, the distal cover 292 may comprise a tube or a longitudinally slit tube, and the first section 292a can include two or more semi-cylindrical or partially cylindrical strips or tube portions separated by a corresponding number of generally parallel, longitudinally oriented cuts or separations formed or otherwise positioned in the sidewall of the tube. Therefore, when in the pre-expansion state, as shown in FIGS. 2-4, the first section 292a may generally have the shape of a longitudinally split or longitudinally slotted tube extending or interposed radially between the outer surface of the stent or device 200 and the inner surface 218 of the catheter 210.

In various embodiments, the strips, wings, or elongate portions of the first section 292a may collectively span substantially the entire circumference of the outer surface of the stent 201 (e.g., where the cuts between the strips are splits of substantially zero width), or be sized somewhat less than the entire circumference (e.g., where the cuts between the strips are slots having a nonzero width). In accordance with some embodiments, the width of the strips, wings, or elongate portions of the first section 292a can be between about 0.5 mm and about 4 mm. The width can be about 0.5 mm to about 1.5 mm. In accordance with some embodiments, the width can be about 1 mm.

The strips, wings, or elongate portions of the first section 292a can also extend longitudinally over at least a portion of the distal portion of the stent 201. In various embodiments, the first section 292a can extend between about 1 mm and about 3 mm, or between about 1.5 mm and about 2.5 mm, or about 2 mm, over the distal portion of the stent.

The first section 292a and the second section 292b can define a total length of the distal cover 292. In some embodiments, the total length can be between about 4 mm and about 10 mm. The total length can also be between about 5.5 mm and about 8.5 mm. In some embodiments, the total length can be about 7 mm.

The strips of the first section 292a may be of substantially uniform size. For example, the first section 292a can comprise two strips spanning approximately 180 degrees each, three strips spanning approximately 120 degrees each, four strips spanning approximately 90 degrees each, or otherwise be divided to collectively cover all or part of the circumference of the stent, etc. Alternatively, the strips may differ in angular sizing and coverage area without departing from the scope of the disclosure. In one embodiment, only two strips or tube portions are employed in the first section 292a. The use of only two strips can facilitate radial expansion, distal movement and/or fold-over or everting of the first section 192a, as discussed herein, while minimizing the number of free or uncontained strips in the blood vessel lumen and any potential for injuring the vessel by virtue of contact between a strip and the vessel wall.

The distal cover 292 can be manufactured using a lubricious and/or hydrophilic material such as PTFE or Teflon®, but may be made from other suitable lubricious materials or lubricious polymers. The distal cover can also comprise a radiopaque material which can be blended into the main material (e.g., PTFE) to impart radiopacity. The distal cover 292 can have a thickness of between about 0.0005" and about 0.003". In some embodiments, the distal cover can be one or more strips of PTFE having a thickness of about 0.001".

The distal cover 292 (e.g., the second end 292b thereof) can be fixed to the core member 260 (e.g., to the distal wire 272 or distal tip 264 thereof) so as to be immovable relative to the core member 260, either in a longitudinal/sliding manner or a radial/rotational manner. Alternatively, as depicted in FIGS. 2-4, the distal cover 292 (e.g., the second end 292b thereof) can be coupled to (e.g., mounted on) the core member 260 so that the distal cover 292 can rotate about the longitudinal axis A-A of the core member 260 (e.g., of the distal wire 272), and/or move or slide longitudinally along the core member. In such embodiments, the second end 292b can have an inner lumen that receives the core member 260 therein such that the distal cover 292 can slide and/or rotate relative to the core member 260. Additionally in such embodiments, the distal coupling unit 290 can further comprise a proximal restraint 294 that is fixed to the core member 260 and located proximal of the (second end 292b of the) distal cover 292, and/or a distal restraint 296 that is fixed to the core member 260 and located distal of the (second end 292b of the) distal cover 292. The proximal and distal restraints 294, 296 can be spaced apart along the core member 260 by a longitudinal distance that is slightly greater than the length of the second end 292b, so as to leave one or more longitudinal gaps 297 between the second end 292b and one or both of the proximal and distal restraints 194, 196, depending on the position of the second end 292b between the restraints. When present, the longitudinal gap(s) 197 allow the second end 292b and/or distal cover 292 to slide longitudinally along the core member 260 between the restraints 294, 296. The longitudinal range of motion of the second end 292b and/or distal cover 292 between the restraints 294, 296 is approximately equal to the total length of the longitudinal gap(s) 297.

Instead of or in addition to the longitudinal gap(s) 297, the distal coupling unit 290 can comprise a radial gap 298 between the outer surface of the core member 260 (e.g., of the distal wire 272) and the inner surface of the second end 292b. Such a radial gap 298 can be formed when the second end 292b is constructed with an inner luminal diameter that is somewhat larger than the outer diameter of the corresponding portion of the core member 260. When present, the radial gap 298 allows the distal cover 292 and/or second end 292b to rotate about the longitudinal axis A-A of the core member 260 between the restraints 294, 296. The presence of longitudinal gaps 297 of at least a minimal size on either side of the second end 292b can also facilitate the rotatability of the distal cover.

One or both of the proximal and distal restraints 294, 296 can have an outside diameter or other radially outermost dimension that is smaller than the (e.g., pre-deployment) outside diameter or other radially outermost dimension of the distal cover 292, so that one or both of the restraints 294, 296 will tend not to bear against or contact the inner surface 218 of the catheter 210 during operation of the core assembly 240.

In the embodiment depicted in FIGS. 2-4, the second end 292b of the distal cover 292 includes an internal hoop 292c which can comprise a (metallic or polymeric) coil as depicted, or other generally rigid, tubular, or cylindrical internal member such as a short segment of relatively stiff polymeric or metallic tubing. The internal hoop 292c can be contained in an annular enclosure or loop(s) formed by the second end 292b, or otherwise attached to or integrated into the second end 292b in a manner that tends to maintain an inside diameter of the distal cover 292 in the second end 292b that is larger than the outside diameter of the adjacent portion of the core member 160 (or the wire 172 thereof). In other words, the hoop 292c can help maintain the presence of the radial gap 298 between the inside diameter of the second end 292b and the outside diameter of the core member 260 or distal wire 272.

The annular enclosure or loop(s) of the second end 292b can be formed by wrapping a portion of a sheet or tube of the distal cover material (e.g., PTFE) around the sidewall and through the lumen of the hoop 292c and adhering, gluing or heat bonding an end of the wrapped portion of the sheet or tube to the adjacent, proximally extending portion of the sheet or tube. Thus are formed two layers that are adhered together on the proximal side of the hoop 292c. Where the distal cover material comprises PTFE, unsintered PTFE can be used to enable bonding the two portions of the material together with heat and pressure, which is not typically possible with "ordinary" or sintered PTFE.

In operation, the distal cover 292, and in particular the first section 192a, can generally cover and protect the distal region 304 of the stent 201 as the stent 201 is moved distally within the catheter 110. The distal cover 192 may serve as a bearing or buffer layer that, for example, inhibits filament ends of the distal region 304 of the stent 201 (where the stent 201 comprises a braided stent) from contacting the inner surface 118 of the catheter 110, which could damage the stent 201 and/or catheter 110, or otherwise compromise the structural integrity of the stent 201. Since the distal cover 192 may be made of a lubricious material, the distal cover 192 may exhibit a low coefficient of friction that allows the distal region 304 of the stent 201 to slide axially within the catheter 110 with relative ease. The coefficient of friction between the distal cover and the inner surface of the catheter can be between about 0.02 and about 0.4. For example, in embodiments in which the distal cover and the catheter are formed from PTFE, the coefficient of friction can be about 0.04. Such embodiments can advantageously improve the ability of the core assembly to pass through the catheter, especially in tortuous vasculature.

Further, as shown in FIGS. 2-4, at least a portion of the distal cover 292 can at least partially extend or be interposed radially between the distal portion of the stent 201 and the inner surface 218 of the catheter 210 in the first position, configuration, or orientation. In the first orientation, the first section 292a of the distal cover 292 can extend from the second section 292b in a proximal direction to a point where the first section is interposed between the distal portion of the stent 201 and the inner surface 218 of the catheter 210. In this orientation, the first section of the distal cover can take on a "proximally oriented" position or configuration.

Structures other than the herein-described embodiments of the distal cover 292 may be used in the core assembly 240 and/or distal coupling unit 290 to cover or otherwise interface with the distal region 304 of the stent 201. For example, a protective coil or other sleeve having a longitudinally oriented, proximally open lumen may be employed. In other embodiments, the distal coupling unit 290 can omit the distal cover 292, or the distal cover can be replaced with a component similar to the proximal coupling unit 282. Where the distal cover 292 is employed, it can be connected to the distal tip coil 265 (e.g., by being wrapped around and enclosing some or all of the winds of the coil 265) or being adhered to or coupled to the outer surface of the coil by an adhesive or a surrounding shrink tube. The distal cover 292 can be coupled (directly or indirectly) to other portions of the core assembly 240, such as the distal wire 272.

In embodiments of the core assembly 240 that employ both a rotatable proximal coupling unit 282 and a rotatable distal cover 292, the stent 201 can be rotatable with respect to the core member 260 about the longitudinal axis A-A thereof, by virtue of the rotatable (connections of the) proximal coupling unit 282 and distal cover 292. In such embodiments, the stent 201, proximal coupling unit 282 and distal cover 292 can rotate together in this manner about the core member. When the stent 201 can rotate about the core member 260, the core assembly 240 can be advanced more easily through tortuous vessels as the tendency of the vessels to twist the stent and/or core assembly is negated by the rotation of the stent, proximal engagement member and distal cover about the core member. In addition, the required push force or delivery force is reduced, as the user's input push force is not diverted into torsion of the stent and/or core member. The tendency of a twisted stent and/or core member to untwist suddenly or "whip" upon exiting tortuosity or deployment of the stent, and the tendency of a twisted stent to resist expansion upon deployment, are also reduced or eliminated. Further, in some such embodiments of the core assembly 240, the user can "steer" the core assembly 240 via the tip coil 265, particularly if the coil 265 is bent at an angle in its unstressed configuration. Such a coil tip can be rotated about the axis A-A relative to the stent 201, coupling unit 282 and/or distal cover 292 by rotating the distal region 264 of the core member 260. Thus the user can point the coil tip in the desired direction of travel of the core assembly, and upon advancement of the core assembly the tip will guide the core assembly in the chosen direction.

Figure 5A:
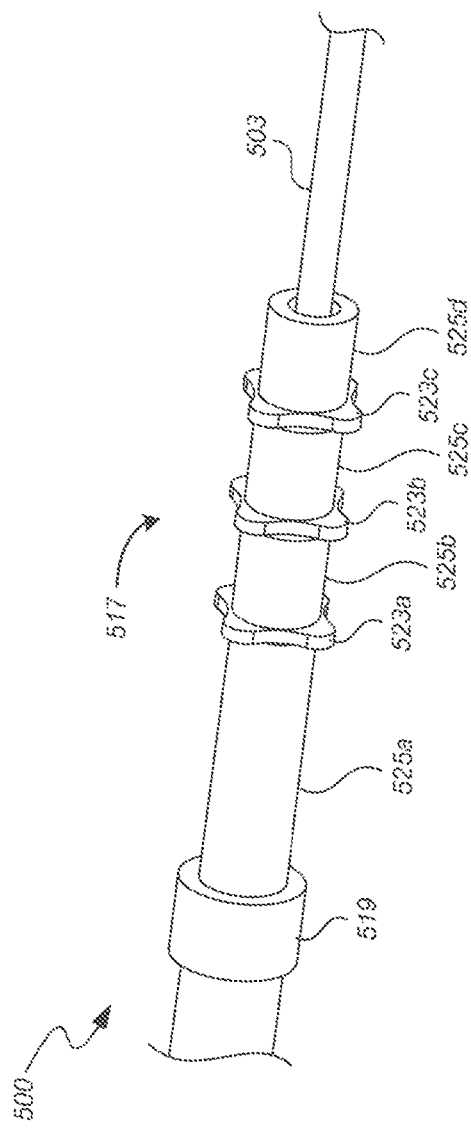
FIG. 5A is an enlarged perspective view of a coupling unit having couplers in accordance with some embodiments.
Figure 5B:
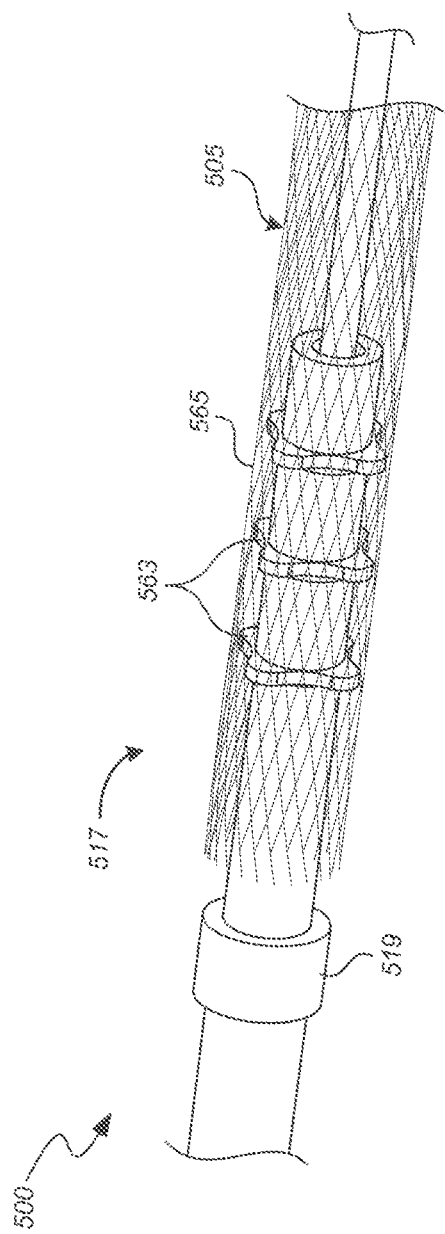
FIG. 5B is an enlarged perspective view of the coupling unit of FIG. 5A with an overlying stent.
Figure 6B:
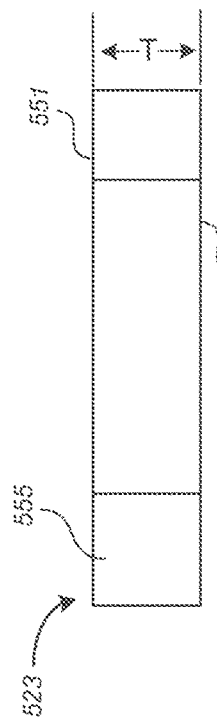
FIGS. 6A-6C are side, end, and perspective views, respectively, of an individual coupler of the coupling unit of FIGS. 5A and 5B.
Figure 6C:
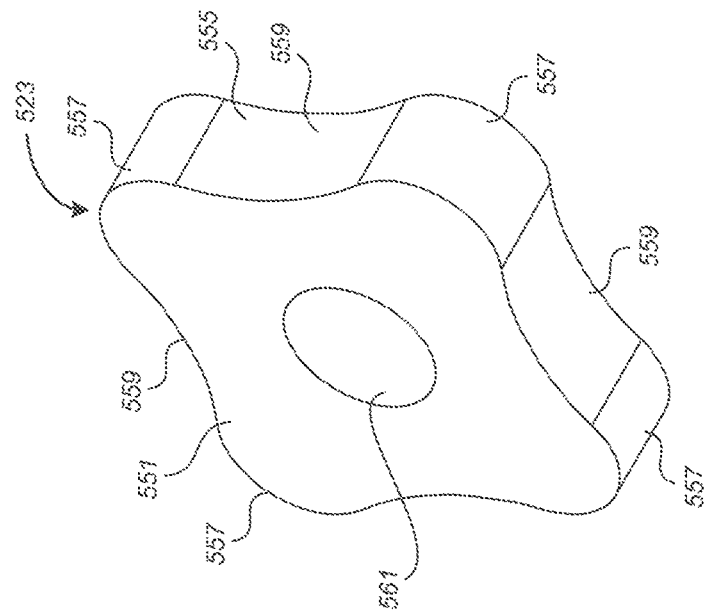
Figure 6A:
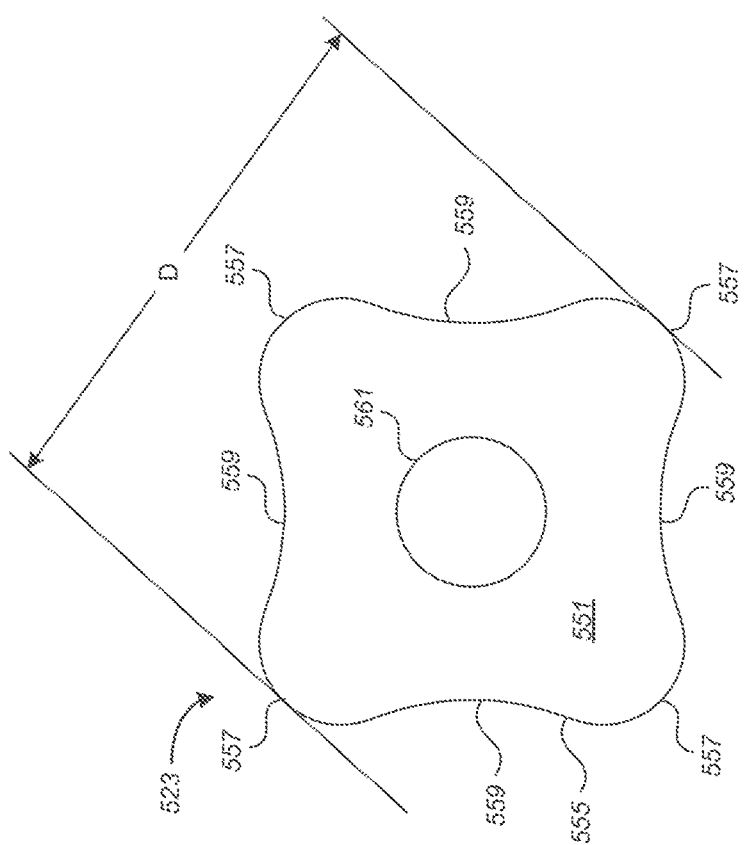
Figure 7:
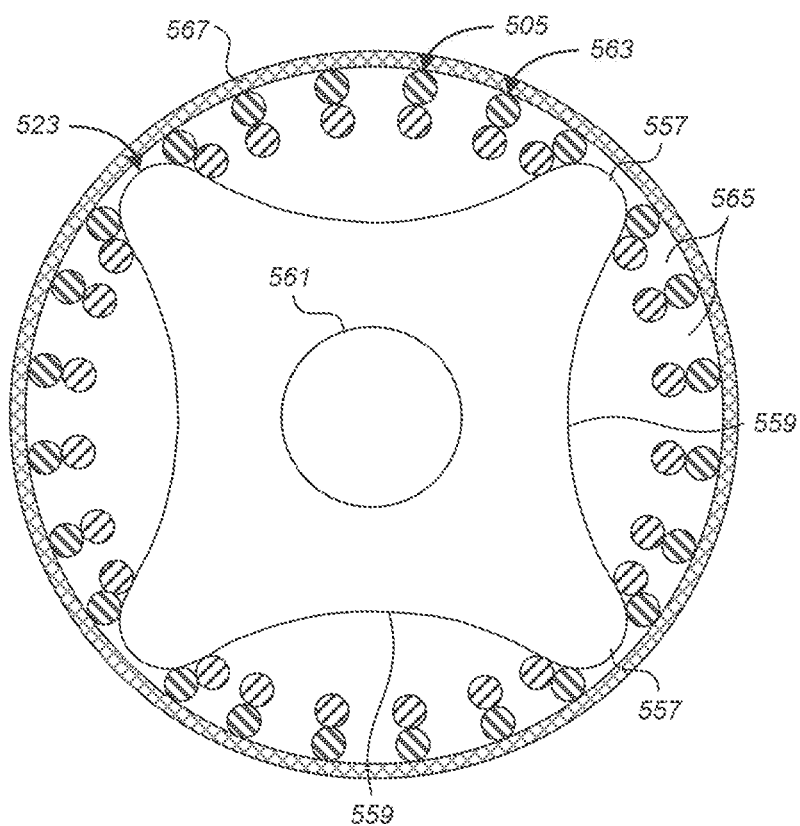
FIG. 7 is a schematic cross-sectional view of a coupler and the stent of FIG. 5B.

FIG. 5A is an enlarged perspective view of a coupling unit 517 of a medical device delivery system 500. FIG. 5B illustrates the coupling unit 517 with an overlying stent 505. The coupling unit 517 includes a plurality of couplers 523a-c separated by a plurality of spacers 525a-d. A proximal restraint 519 is disposed proximally to the proximal-most spacer 525a. The proximal restraint 519 and the coupling unit 517 are disposed around the core member 503. FIGS. 6A-6C are side, end, and perspective views, respectively, of a coupler 523 of the coupling unit 517 shown in FIGS. 5A and 5B. FIG. 7 is a schematic cross-sectional view of the coupler 523 engaging the stent 505. The depicted stent 505 is braided (although other types of stent, as disclosed elsewhere herein may be used) and includes a mesh 563 forming a plurality of pores 565 which are separated by points where the wires of the braid cross or intersect.

Referring to FIGS. 5A-7 together, each of the couplers 523 can have a plate-like configuration with first and second end faces 551, 553 and a side surface 555 extending between the first and second end faces 551, 553. In the assembled delivery system 500, the first and second end faces 551, 553 can be oriented and maintained substantially orthogonal to a long axis of the core member 503. This can be achieved by configuring the spacers 525a-d with distal and proximal end faces that are orthogonal to the longitudinal axis of each spacer 525 (and/or to the core member 503), and/or minimizing the amount of longitudinal movement space (or "play") among the couplers and spacers of the coupling unit 517. Each coupler forms a plurality of radially-extending projections 557 separated by recesses 559. In the illustrated embodiment, there are four projections 557 separated by four recesses 559. However, in other embodiments the number of projections can vary, for example two, three, four, five, six, seven, or more projections separated by a corresponding number of recesses.

The projections 557 can include rounded edges and the recesses 559 can include rounded depressions. During use of the delivery system 500, the rounded edges can reduce scraping of the projections 557 against the inner wall of an overlying catheter 567, which reduces generation of particulates and damage to the catheter 567. When the delivery system 500 is used with a braided stent such as the depicted stent 505, the recesses 559 can be sized to accommodate the thickness of braid wire crossings such that each projection can extend at least partially into a pore 565 of the stent 505 between the adjacent wire crossings and the wire crossings surrounding the pore 565 can be at least partially received within the recesses 559 of the coupler. In other embodiments, the projections and/or the recesses can assume other forms, for example with sharper or flatter peaks formed by the projections. The coupler 523 can be manufactured by photochemical etching, laser cutting, molding, machining or other suitable processes.

Each coupler 523 includes an opening or central aperture 561 configured to receive the core member 503 therethrough. As noted previously, the opening of the aperture 561 can be larger than the diameter of the core member 503 such that the couplers 523 can rotate about the long axis of the core member 503.

The couplers 523 can be made to have a relatively thin and/or plate-like configuration. Such a configuration can facilitate the formation of projections 557 that are small enough to fit inside the pores 565 of the stent 505. Accordingly, the couplers 523 may be characterized by a largest diameter D along the first and second end faces 551, 553, and a thickness T measured along the side surface 555. In some embodiments, the diameter D is at least five times greater than the thickness T. In at least one embodiment, the thickness T is between approximately 25-100 microns, or 25-75 microns, for example, approximately 50 microns (approximately 0.002").

In order to effectively push or pull the stent 505 along the catheter 567, the couplers 523 can be made to be rigid (e.g., incompressible by the forces encountered in typical use of the delivery system). The rigidity of the couplers 523 can be due to their material composition, their shape/construction, or both. In some embodiments, the couplers 523 are made of metal (e.g., stainless steel, Nitinol, etc.) or rigid polymers (e.g., polyimide), or both. In some embodiments, even if the coupler is made of a rigid material, based on structural characteristics the coupler itself may be non-rigid and at least partially compressible.

The spacers 525 can be substantially cylindrical bodies having a smaller outer diameter than a largest outer diameter of the couplers 523. In some embodiments, the spacers 525 include a central aperture (not shown) sized and configured to allow the spacers 525 to be rotatably mounted over the core member 503. As mentioned previously, the spacers 525 can have end walls that are orthogonal to a long axis of the core member 503. These orthogonal end walls can help preserve the orthogonal orientation of the couplers 523 relative to the core member 503 to prevent loss of engagement with stent 505.

In some embodiments, the coupling unit 517 can be configured to engage only a proximal portion (e.g., only a proximal half, only the proximal-most third, etc.) of the stent 505. In other embodiments, coupling unit 517 can engage the stent 505 along substantially its entire length.

The couplers 523 can mechanically interlock with or engage the stent 505 such that each projection 557 is at least partially received within one of the pores 565. The spacers can be configured with a length such that the projections 557 of adjacent couplers 523 (e.g., coupler 523a and adjacent coupler 523b) are spaced apart longitudinally by a distance that is equal to the "pore pitch" of the stent 505 (the distance between the centers of longitudinally adjacent pores 565) or, more typically, a whole-number multiple of the pore pitch of the stent 505, when the stent is at the inner diameter of the catheter 567. Accordingly, each projection can extend into and engage one of the pores 565 of the stent 505. In some embodiments, adjacent couplers 523 can engage longitudinally adjacent pores 565 of the stent 505; in other embodiments adjacent couplers 523 engage pores 565 which are not longitudinally adjacent but are spaced apart longitudinally by one or more intervening pores. Therefore the first and second couplers 523a and 523b can be spaced apart from one another by a longitudinal distance corresponding to the pore pitch of the stent 505, or by a longitudinal distance corresponding to a whole number multiple of the pore pitch.

The interaction between the projections 557 and the pores 565 can produce a mechanical interlock between stent coupler 523 and the pores 565. This is in contrast to a conventional compressible pad that resiliently pushes against the stent as a whole, including the wire crossings. In at least some embodiments, the mechanical interlock provided by the couplers 523 secures the stent 505 without pressing against the wire crossings of the stent 505. In some embodiments, the couplers 523 are configured to secure a range of different stent sizes within a given catheter size (e.g., within a 0.017", 0.021" or 0.027" catheter (inside diameter)).

Note that various components of the delivery system 500 of FIGS. 5A-7 can be incorporated into the delivery system 100 of FIG. 1, or into the delivery system 200 of FIGS. 2-4. For example, any of the disclosed embodiments of the coupling unit 517 can be employed as the coupling unit of the delivery system 100 or of the delivery system 200. Similarly, any of the embodiments of the couplers 523 can be employed as the coupler(s) of the delivery system 100 or of the delivery system 200, and/or any of the embodiments of the spacers 525 can be employed as the spacer(s) of the delivery system 100 or of the delivery system 200.

CONCLUSION

This disclosure is not intended to be exhaustive or to limit the present technology to the precise forms disclosed herein. Although specific embodiments are disclosed herein for illustrative purposes, various equivalent modifications are possible without deviating from the present technology, as those of ordinary skill in the relevant art will recognize. In some cases, well-known structures and functions have not been shown and/or described in detail to avoid unnecessarily obscuring the description of the embodiments of the present technology. Although steps of methods may be presented herein in a particular order, in alternative embodiments the steps may have another suitable order. Similarly, certain aspects of the present technology disclosed in the context of particular embodiments can be combined or eliminated in other embodiments. Furthermore, while advantages associated with certain embodiments may have been disclosed in the context of those embodiments, other embodiments can also exhibit such advantages, and not all embodiments need necessarily exhibit such advantages or other advantages disclosed herein to fall within the scope of the present technology. Accordingly, this disclosure and associated technology can encompass other embodiments not expressly shown and/or described herein.

Throughout this disclosure, the singular terms "a," "an," and "the" include plural referents unless the context clearly indicates otherwise. Similarly, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the terms "comprising" and the like are used throughout this disclosure to mean including at least the recited feature(s) such that any greater number of the same feature(s) and/or one or more additional types of features are not precluded. Directional terms, such as "upper," "lower," "front," "back," "vertical," and "horizontal," may be used herein to express and clarify the relationship between various elements. It should be understood that such terms do not denote absolute orientation. Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics may be combined in any suitable manner in one or more embodiments.

We claim:

1. A stent delivery system, comprising:
   a core member having a distal segment;
   a coupling unit positioned about the core member distal segment, the coupling unit comprising:
      a proximal restraint coupled to the core member distal segment;
      a distal restraint coupled to the core member distal segment at a position distal to the proximal restraint;
      two or more plates slidably coupled to the core member distal segment between the proximal restraint and the distal restraint; and
      one or more spacers coupled to the core member distal segment between the proximal restraint and the distal restraint,
      wherein the proximal restraint and the distal restraint are spaced apart along the core member by a longitudinal distance that is greater than the combined length of the two or more plates and the one or more spacers coupled to the core member distal segment between the proximal restraint and the distal restraint; and
   a stent extending along the core member distal segment such that an inner surface of the stent is engaged by at least one of the plates.

2. The stent delivery system of claim 1, wherein the longitudinal distance is such that plates can slide longitudinally along the core member distal segment with respect to the proximal and distal restraints.

3. The stent delivery system of claim 1, wherein the one or more spacers comprises a spacer disposed between two plates.

4. The stent delivery system of claim 1, wherein:
   the two or more plates comprise first, second, and third plates,
   the one or more spacers comprise first and second spacers, and
   the first spacer is disposed between the first and second plates and the second spacer is disposed between the second and third plates.

5. The stent delivery system of claim 4, wherein the proximal restraint and the distal restraint are spaced apart along the core member by a longitudinal distance that is greater than the combined length of the first, second, and third plates and the first and second spacers.

6. The stent delivery system of claim 1, wherein at least one projection of the two or more plates is interlocked with the stent such that the projection is at least partially received within a pore of the stent.

7. The stent delivery system of claim 1, wherein the two or more plates are spaced apart from one another by a distance corresponding to a distance between centers of longitudinally adjacent pores of the stent.

8. A stent delivery system, comprising:
   a catheter having a lumen and an inner surface extending along the lumen;
   a core member, extending within the catheter lumen;
   first and second couplers slidably mounted to the core member, each of the first and second couplers comprising:
      a first end surface, a second end surface, and a side surface extending between the first end surface and the second end surface; and
      an aperture extending through the first and second end surfaces, the core member and extending through the aperture, the aperture defining a radial gap between an outer surface of the core member and an inner surface of the coupler;
   one or more spacers mounted on the core member;
   a proximal restraint mounted on the core member at a position proximal to the first coupler, the second coupler, and the one or more spacers;
   a distal restraint mounted on the core member at a position distal to the first coupler, the second coupler, and the one or more spacers, the distal restraint spaced apart from the proximal restraint by a longitudinal distance greater than the combined length of the first and second couplers and the one or more spacers; and
   a stent extending along the core member and disposed radially between the catheter inner surface and the first and second couplers.

9. The stent delivery system of claim 8, wherein the stent comprises a mesh forming a plurality of pores, and wherein the first and second couplers are spaced apart from one another by a distance corresponding to a distance between centers of longitudinally adjacent pores of the stent.

10. The stent delivery system of claim 8, wherein a radially outermost dimension of the spacer is smaller than a radially outermost dimension of the first coupler and the second coupler.

11. The stent delivery system of claim 8, wherein the one or more spacers are fixed with respect to the core member.

12. The stent delivery system of claim 8, wherein the one or more spacers comprises a spacer disposed between the first coupler and the second coupler.

13. The stent delivery system of claim 8, further comprising a third coupler slidably mounted to the core member, wherein:
   the one or more spacers comprise first and second spacers, and
   the first spacer is disposed between the first and second couplers and the second spacer is disposed between the second and third couplers.

14. The stent delivery system of claim 8, wherein a side surface of the first coupler and a side surface of the second coupler each comprise one or more projections separated by recesses.

15. An assembly configured to engage a stent, comprising:
a core member;
a proximal restraint mounted on the core member;
a distal restraint mounted on the core member at a position distal the proximal restraint;
a first coupler slidably coupled to the core member between the proximal restraint and the distal restraint;
a second coupler slidably coupled to the core member at a position between the proximal restraint and the distal restraint; and
one or more spacers coupled to the core member at a position between the proximal restraint and the distal restraint,
wherein the proximal and distal restraints are spaced apart along the core member by a longitudinal distance that is greater than a combined length of the first and second couplers and the one or more spacers.

16. The assembly of claim 15, wherein a radially outermost dimension of the spacer is smaller than a radially outermost dimension of the first coupler and the second coupler.

17. The assembly of claim 15, wherein the one or more spacers comprises a spacer disposed between the first couplers and the second coupler.

18. The assembly of claim 15, wherein the first coupler and the second coupler each comprise:
a first end surface, a second end surface, and a side surface comprising one or more projections extending between the first end surface and the second end surface; and
an aperture extending through the first and second end surfaces, the core member extending through the aperture, the aperture defining a radial gap between an outer surface of the core member and an inner surface of the coupler.

19. The assembly of claim 18, wherein the projections comprise rounded edges.

20. The assembly of claim 15, wherein the one or more spacers comprises a spacer disposed between first and second couplers.

21. The assembly of claim 15, further comprising a third coupler slidably mounted to the core member, wherein:
the one or more spacers comprise first and second spacers, and
the first spacer is disposed between the first and second couplers and the second spacer is disposed between the second and third couplers.

22. The assembly of claim 21, wherein the proximal restraint and the distal restraint are spaced apart along the core member by a longitudinal distance that is greater than the combined length of the first, second, and third couplers and the first and second spacers.

* * * * *

UNITED STATES PATENT AND TRADEMARK OFFICE
CERTIFICATE OF CORRECTION

PATENT NO. : 10,945,867 B2  
APPLICATION NO. : 16/459118  
DATED : March 16, 2021  
INVENTOR(S) : Nageswaran et al.

Page 1 of 1

It is certified that error appears in the above-identified patent and that said Letters Patent is hereby corrected as shown below:

On the Title Page

Item (57), Column 2, in "Abstract", Line 4, after "segment." delete "the" and insert -- The --, therefor.

In the Claims

In Column 17, in Claim 1, Line 41, after "restraint" delete "," and insert -- ; --, therefor.

In Column 19, in Claim 17, Lines 23-24, delete "couplers" and insert -- coupler --, therefor.

Signed and Sealed this  
Twenty-seventh Day of April, 2021

Drew Hirshfeld  
*Performing the Functions and Duties of the*  
*Under Secretary of Commerce for Intellectual Property and*  
*Director of the United States Patent and Trademark Office*